US008829282B2

(12) United States Patent
Lisieczko

(10) Patent No.: US 8,829,282 B2
(45) Date of Patent: Sep. 9, 2014

(54) PLANTS AND SEEDS OF SPRING CANOLA VARIETY SCV425044

(75) Inventor: Zenon Lisieczko, Guelph (CA)

(73) Assignee: Monsanto Technology, LLC, St. Louis, MO (US)

( * ) Notice: Subject to any disclaimer, the term of this patent is extended or adjusted under 35 U.S.C. 154(b) by 306 days.

(21) Appl. No.: 12/120,297

(22) Filed: May 14, 2008

(65) Prior Publication Data

US 2009/0285967 A1  Nov. 19, 2009

(51) Int. Cl.
A01H 5/00 (2006.01)
A01H 5/10 (2006.01)
A01H 1/00 (2006.01)
C12N 15/82 (2006.01)

(52) U.S. Cl.
USPC ............................ 800/306; 800/260; 435/430

(58) Field of Classification Search
None
See application file for complete search history.

(56) References Cited

U.S. PATENT DOCUMENTS

| 3,710,511 A | 1/1973 | Patterson |
| 3,861,709 A | 1/1975 | Mulcahy et al. |
| 4,535,060 A | 8/1985 | Comai |
| 4,654,465 A | 3/1987 | Brar et al. |
| 4,658,085 A | 4/1987 | Beversdorf et al. |
| 4,727,219 A | 2/1988 | Brar et al. |
| 4,769,061 A | 9/1988 | Comai |
| 4,810,648 A | 3/1989 | Stalker |
| 4,940,835 A | 7/1990 | Shah et al. |
| 4,971,908 A | 11/1990 | Kishore et al. |
| 4,975,374 A | 12/1990 | Goodman et al. |
| 5,015,580 A | 5/1991 | Christou et al. |
| 5,034,323 A | 7/1991 | Jorgensen et al. |
| 5,107,065 A | 4/1992 | Shewmaker et al. |
| 5,145,783 A | 9/1992 | Kishore et al. |
| 5,188,642 A | 2/1993 | Shah et al. |
| 5,266,317 A | 11/1993 | Tomalski et al. |
| 5,310,667 A | 5/1994 | Eischholtz et al. |
| 5,312,910 A | 5/1994 | Kishore et al. |
| 5,322,783 A | 6/1994 | Tomes et al. |
| 5,432,068 A | 7/1995 | Albertsen et al. |
| 5,453,566 A | 9/1995 | Shewmaker et al. |
| 5,463,175 A | 10/1995 | Barry et al. |
| 5,478,369 A | 12/1995 | Albertsen et al. |
| 5,491,288 A | 2/1996 | Chaubet et al. |
| 5,494,813 A | 2/1996 | Hepher et al. |
| 5,510,471 A | 4/1996 | Lebrun et al. |
| 5,559,223 A | 9/1996 | Falco et al. |
| 5,563,055 A | 10/1996 | Townsend et al. |
| 5,607,914 A | 3/1997 | Rao et al. |
| 5,627,061 A | 5/1997 | Barry et al. |
| 5,633,435 A | 5/1997 | Barry et al. |
| 5,633,436 A | 5/1997 | Wandelt |
| 5,633,448 A | 5/1997 | Lebrun et al. |
| 5,759,829 A | 6/1998 | Shewmaker et al. |
| 5,767,373 A | 6/1998 | Ward et al. |
| 5,776,760 A | 7/1998 | Barry et al. |
| 5,789,566 A | 8/1998 | Bonhomme et al. |
| 5,792,931 A | 8/1998 | Duvick et al. |
| 5,804,425 A | 9/1998 | Barry et al. |
| 5,824,524 A | 10/1998 | Albertsen et al. |
| 5,850,014 A | 12/1998 | Albertsen et al. |
| 5,850,016 A | 12/1998 | Jung et al. |
| 5,859,341 A | 1/1999 | Albertsen et al. |
| 5,866,775 A | 2/1999 | Eichholtz et al. |
| 5,885,801 A | 3/1999 | Rao |
| 5,885,802 A | 3/1999 | Rao |
| 5,891,859 A | 4/1999 | Thomashow et al. |
| 5,892,009 A | 4/1999 | Thomashow et al. |
| 5,912,414 A | 6/1999 | Falco et al. |
| 5,929,305 A | 7/1999 | Thomashow et al. |
| 5,939,599 A | 8/1999 | Chui et al. |
| 5,959,185 A | 9/1999 | Streit et al. |
| 5,965,705 A | 10/1999 | Thomashow et al. |
| 5,973,233 A | 10/1999 | Burns et al. |
| 5,973,234 A | 10/1999 | Mueller et al. |

(Continued)

FOREIGN PATENT DOCUMENTS

| EP | 0333033 A1 | 9/1989 |
| EP | 0242236 A1 | 10/1990 |

(Continued)

OTHER PUBLICATIONS

Canadian Intellectual Property Office, Office Action issued Aug. 27, 2013 in Canadian Application No. 2,696,355, filed Mar. 10, 2010, Monsanto Technology LLC.
Canadian Intellectual Property Office, Office Action issued Mar. 6, 2014 in Canadian Application No. 2,665,608, filed May 7, 2009, Monsanto Technology LLC.
Canadian Intellectual Property Office, Office Action issued Mar. 7, 2014 in Canadian Application No. 2,665,606, filed May 7, 2009, Monsanto Technology LLC.
Canadian Intellectual Property Office, Office Action issued Mar. 10, 2014 in Canadian Application No. 2,665,613, filed May 7, 2009, Monsanto Technology LLC.
Canadian Intellectual Property Office, Office Action issued Mar. 10, 2014 in Canadian Application No. 2,665,610, filed May 7, 2009, Monsanto Technology LLC.
Canadian Intellectual Property Office, Office Action issued Mar. 13, 2014 in Canadian Application No. 2,726,403, filed Dec. 23, 2010, Monsanto Technology LLC.
Sasongko, N.D. et al., "Toward Increasing Erucic Acid Content in Oilseed Rape (*Brassica napus* L.) Through the Combination with Genes for High Oleic Acid," Journal of the American Oil Chemists' Society, 2005, pp. 445-449, 82/6.
Response to Office Action, filed Jan. 18, 2012, with the United States Patent and Trademark Office, in response to the outstanding Non-Final Office Action, mailed Dec. 29, 2011, U.S. Appl. No. 12/713,411, filed Feb. 26, 2010, Jun Liu.

(Continued)

Primary Examiner — Elizabeth McElwain
(74) Attorney, Agent, or Firm — Nelson Mullins Riley & Scarborough LLP

(57) ABSTRACT

A canola line designated SCV425044 is disclosed. The invention relates to the seeds of canola line SCV425044, to the plants of canola SCV425044, to plant parts of canola line SCV425044 and to methods for producing a canola plant produced by crossing canola line SCV425044 with itself or with another canola line. The invention also relates to methods for producing a canola plant containing in its genetic material one or more transgenes and to the transgenic canola plants and plant parts produced by those methods. This invention also relates to canola lines or breeding lines and plant parts derived from canola line SCV425044, to methods for producing other canola lines, lines or plant parts derived from canola line SCV425044 and to the canola plants, varieties, and their parts derived from use of those methods. The invention further relates to hybrid canola seeds, plants and plant parts produced by crossing the line SCV425044 with another canola line.

25 Claims, No Drawings

(56) References Cited

U.S. PATENT DOCUMENTS

| | | |
|---|---|---|
| 5,977,445 A | 11/1999 | Soper et al. |
| 5,990,389 A | 11/1999 | Rao et al. |
| RE36,449 E | 12/1999 | Lebrun et al. |
| 6,040,497 A | 3/2000 | Spencer et al. |
| 6,063,947 A | 5/2000 | DeBonte et al. |
| 6,080,913 A | 6/2000 | Tarczynski et al. |
| 6,084,153 A | 7/2000 | Good et al. |
| 6,107,547 A | 8/2000 | Coruzzi et al. |
| 6,118,055 A | 9/2000 | Livesey |
| 6,127,600 A | 10/2000 | Beach et al. |
| 6,130,366 A | 10/2000 | Herrera-Estrella et al. |
| 6,162,967 A | 12/2000 | Webb |
| 6,177,275 B1 | 1/2001 | Coruzzi et al. |
| 6,194,638 B1 | 2/2001 | Dhugga et al. |
| 6,197,561 B1 | 3/2001 | Martino-Catt et al. |
| 6,225,114 B1 | 5/2001 | Eichholtz et al. |
| 6,229,072 B1 | 5/2001 | Burns et al. |
| 6,232,529 B1 | 5/2001 | Singletary et al. |
| 6,248,876 B1 | 6/2001 | Barry et al. |
| RE37,287 E | 7/2001 | Lebrun et al. |
| 6,265,640 B1 | 7/2001 | Albertsen et al. |
| 6,282,837 B1 | 9/2001 | Ward et al. |
| 6,288,306 B1 | 9/2001 | Ward et al. |
| 6,291,224 B1 | 9/2001 | Martin-Catt et al. |
| 6,297,426 B1 | 10/2001 | Albertsen et al. |
| 6,307,126 B1 | 10/2001 | Harberd et al. |
| 6,323,392 B1 | 11/2001 | Charne |
| 6,338,961 B1 | 1/2002 | DeRose et al. |
| 6,346,403 B1 | 2/2002 | Rafalski et al. |
| 6,391,348 B1 | 5/2002 | Stilborn et al. |
| 6,399,859 B1 | 6/2002 | Nichols et al. |
| 6,417,428 B1 | 7/2002 | Thomashow et al. |
| 6,423,886 B1 | 7/2002 | Singletary et al. |
| 6,441,274 B1 | 8/2002 | Cahoon et al. |
| 6,459,019 B1 | 10/2002 | Falco et al. |
| 6,563,020 B1 | 5/2003 | Simmons et al. |
| 6,566,587 B1 | 5/2003 | Lebrun et al. |
| 6,573,430 B1 | 6/2003 | Bradley et al. |
| 6,664,445 B1 | 12/2003 | Falco et al. |
| 6,664,446 B2 | 12/2003 | Heard et al. |
| 6,706,866 B1 | 3/2004 | Thomashow et al. |
| 6,713,663 B2 | 3/2004 | Weigel et al. |
| 6,717,034 B2 | 4/2004 | Jiang |
| 6,787,683 B1 | 9/2004 | Penna et al. |
| 6,794,560 B2 | 9/2004 | Harberd et al. |
| 6,801,104 B2 | 10/2004 | Zhu et al. |
| 6,803,498 B2 | 10/2004 | Dhugga et al. |
| 6,825,397 B1 | 11/2004 | Lowe et al. |
| 6,858,778 B1 | 2/2005 | Jung et al. |
| 6,875,907 B2 | 4/2005 | Simmons et al. |
| 6,911,577 B2 | 6/2005 | Simmons et al. |
| 6,930,225 B2 | 8/2005 | Dhugga et al. |
| 6,992,237 B1 | 1/2006 | Habben et al. |
| 7,067,720 B2 | 6/2006 | Shi et al. |
| 7,087,810 B2 | 8/2006 | Muller et al. |
| 7,098,381 B2 | 8/2006 | Singletary et al. |
| 7,135,615 B2 | 11/2006 | Kato |
| 7,145,060 B2 | 12/2006 | Muller et al. |
| 7,154,029 B2 | 12/2006 | Cahoon et al. |
| 7,157,621 B2 | 1/2007 | Allen et al. |
| 7,179,955 B2 | 2/2007 | Dhugga et al. |
| 7,205,453 B2 | 4/2007 | Altier et al. |
| 7,288,386 B2 | 10/2007 | Lightfoot et al. |
| 7,462,481 B2 | 12/2008 | Castle et al. |
| 7,531,723 B2 | 5/2009 | Habben et al. |
| 7,723,582 B2 | 5/2010 | Chungu et al. |
| 7,947,877 B2 | 5/2011 | Lisieczko |
| 7,964,744 B2 | 6/2011 | Nara et al. |
| 8,071,848 B2 | 12/2011 | Lisieczko |
| 8,138,394 B2 | 3/2012 | Liu et al. |
| 8,143,488 B2 | 3/2012 | Burns et al. |
| 8,148,611 B2 | 4/2012 | Liu et al. |
| 8,153,865 B2 | 4/2012 | Wu et al. |
| 2003/0079247 A1 | 4/2003 | Shi et al. |
| 2003/0166197 A1 | 9/2003 | Ecker et al. |
| 2004/0068767 A1 | 4/2004 | Dhugga et al. |
| 2004/0078852 A1 | 4/2004 | Thomashow et al. |
| 2004/0098764 A1 | 5/2004 | Heard et al. |
| 2004/0128719 A1 | 7/2004 | Klee et al. |
| 2004/0148654 A1 | 7/2004 | Helentjaris |
| 2005/0160488 A1 | 7/2005 | Jung et al. |
| 2005/0204418 A1 | 9/2005 | Jung et al. |
| 2005/0235383 A1 | 10/2005 | Patel |
| 2005/0278812 A1 | 12/2005 | Patel |
| 2006/0075516 A1 | 4/2006 | Kubik |
| 2006/0075517 A1 | 4/2006 | Kubik |
| 2006/0225146 A1 | 10/2006 | Kubik |
| 2006/0225156 A1 | 10/2006 | Jonsson |
| 2006/0225157 A1 | 10/2006 | Jonsson |
| 2006/0225158 A1* | 10/2006 | Jonsson ............... 800/306 |
| 2006/0225159 A1 | 10/2006 | Kubik |
| 2007/0089181 A1 | 4/2007 | Patel |
| 2008/0256653 A1 | 10/2008 | Chungu et al. |
| 2008/0256654 A1 | 10/2008 | Chungu et al. |
| 2008/0256655 A1 | 10/2008 | Chungu et al. |
| 2008/0256656 A1 | 10/2008 | Chungu et al. |
| 2008/0263714 A1 | 10/2008 | Chungu et al. |
| 2008/0263715 A1 | 10/2008 | Chungu et al. |
| 2008/0263716 A1 | 10/2008 | Chungu et al. |
| 2008/0263717 A1 | 10/2008 | Chungu et al. |
| 2009/0064359 A1 | 3/2009 | Lisieczko |

FOREIGN PATENT DOCUMENTS

| | | |
|---|---|---|
| EP | 0599042 A1 | 10/1993 |
| EP | 1173580 A1 | 1/2002 |
| EP | 1173581 A1 | 1/2002 |
| EP | 1173582 A1 | 1/2002 |
| JP | 2002281975 A | 10/2002 |
| WO | 92/05251 A1 | 4/1992 |
| WO | 92/13956 A1 | 8/1992 |
| WO | 92/13957 A1 | 8/1992 |
| WO | 93/02197 A1 | 2/1993 |
| WO | 93/11245 A1 | 6/1993 |
| WO | 94/00992 A1 | 1/1994 |
| WO | 95/15392 A1 | 6/1995 |
| WO | 95/18855 A2 | 7/1995 |
| WO | 96/01905 A1 | 1/1996 |
| WO | 96/14414 A1 | 5/1996 |
| WO | 96/30530 A1 | 10/1996 |
| WO | 96/38560 A2 | 12/1996 |
| WO | 97/02737 A1 | 1/1997 |
| WO | 97/10339 A1 | 3/1997 |
| WO | 97/29123 A2 | 8/1997 |
| WO | 97/49811 A1 | 12/1997 |
| WO | 98/09521 A1 | 3/1998 |
| WO | 98/20133 A3 | 5/1998 |
| WO | 98/22604 A1 | 5/1998 |
| WO | 98/27806 A1 | 7/1998 |
| WO | 98/42831 A2 | 10/1998 |
| WO | 98/45448 A1 | 10/1998 |
| WO | 98/45458 A1 | 10/1998 |
| WO | 98/53083 A1 | 11/1998 |
| WO | 98/56918 A1 | 12/1998 |
| WO | 98/56935 A2 | 12/1998 |
| WO | 99/05298 A1 | 2/1999 |
| WO | 99/09174 A1 | 2/1999 |
| WO | 99/10498 A2 | 3/1999 |
| WO | 99/25821 A1 | 5/1999 |
| WO | 99/25853 A1 | 5/1999 |
| WO | 99/29882 A1 | 6/1999 |
| WO | 99/38977 A2 | 8/1999 |
| WO | 99/40209 A1 | 8/1999 |
| WO | 99/49064 A2 | 9/1999 |
| WO | 99/53050 A1 | 10/1999 |
| WO | 99/55882 A1 | 11/1999 |
| WO | 00/09706 A2 | 2/2000 |
| WO | 00/31964 A1 | 6/2000 |
| WO | 00/32761 A1 | 6/2000 |
| WO | 00/42219 A1 | 7/2000 |
| WO | 00/44918 A1 | 8/2000 |
| WO | 00/46358 A2 | 8/2000 |
| WO | 00/60089 A1 | 10/2000 |
| WO | 00/68393 A1 | 11/2000 |

(56) References Cited

FOREIGN PATENT DOCUMENTS

| | | |
|---|---|---|
| WO | 00/73475 A1 | 12/2000 |
| WO | 01/04147 A2 | 1/2001 |
| WO | 01/12800 | 2/2001 |
| WO | 01/12825 A1 | 2/2001 |
| WO | 01/21822 A1 | 3/2001 |
| WO | 01/26459 A2 | 4/2001 |
| WO | 01/29237 A2 | 4/2001 |
| WO | 01/34726 A2 | 5/2001 |
| WO | 01/35725 A1 | 5/2001 |
| WO | 01/35727 A1 | 5/2001 |
| WO | 01/36444 A1 | 5/2001 |
| WO | 01/36596 A2 | 5/2001 |
| WO | 01/36598 A1 | 5/2001 |
| WO | 01/52620 A2 | 7/2001 |
| WO | 01/64898 A2 | 9/2001 |
| WO | 01/66704 A2 | 9/2001 |
| WO | 01/79516 A2 | 10/2001 |
| WO | 02/15675 A1 | 2/2002 |
| WO | 02/17430 A1 | 2/2002 |
| WO | 02/42424 A2 | 5/2002 |
| WO | 02/057439 A2 | 7/2002 |
| WO | 02/059324 A2 | 8/2002 |
| WO | 02/002776 A1 | 10/2002 |
| WO | 02/077185 A2 | 10/2002 |
| WO | 02/079403 A2 | 10/2002 |
| WO | 03/000863 A2 | 1/2003 |
| WO | 03/011015 A2 | 2/2003 |
| WO | 03/013227 A2 | 2/2003 |
| WO | 03/013228 A2 | 2/2003 |
| WO | 03/027243 A2 | 4/2003 |
| WO | 03/048345 A1 | 6/2003 |
| WO | 03/052063 A2 | 6/2003 |
| WO | 03/076574 A2 | 9/2003 |
| WO | 03/082899 A2 | 10/2003 |
| WO | 2004/031349 A2 | 4/2004 |
| WO | 2004/076638 A2 | 9/2004 |
| WO | 2004/009143 A2 | 10/2004 |

OTHER PUBLICATIONS

Response to Office Action, filed Jan. 18, 2012, with the United States Patent and Trademark Office, in response to the outstanding Non-Final Office Action, mailed Dec. 29, 2011, U.S. Appl. No. 12/713,479, filed Feb. 26, 2010, Jun Liu.
Response to Office Action, filed Jan. 18, 2012, with the United States Patent and Trademark Office, in response to the outstanding Non-Final Office Action, mailed Dec. 29, 2011, U.S. Appl. No. 12/713,594, filed Feb. 26, 2010, Dale Burns.
Response to Office Action, filed Jan. 18, 2012, with the United States Patent and Trademark Office, in response to the outstanding Non-Final Office Action, mailed Dec. 29, 2011, U.S. Appl. No. 12/721,637, filed Mar. 11, 2010, Chunren Wu.
Response to Office Action, filed Aug. 29, 2012, with the United States Patent and Trademark Office, in response to the outstanding Non-Final Office Action, mailed Jul. 1, 2012, U.S. Appl. No. 12/486,161, filed Jun. 17, 2009, Confirmation No. 4613, Zenon Lisieczko.
Canadian Intellectual Property Office, Office Action, mailed Apr. 2, 2012, Canadian Patent Application No. 2,665,610, filed May 7, 2009, Monsanto Technology LLC.
Canadian Intellectual Property Office, Official Action issued Jul. 10, 2012, Canadian Patent Application No. 2,706,945 filed Jun. 9, 2010, Applicant Monsanto Technology LLC.
Roger N. Beachy, et al., Coat Protein-Mediated Resistance Against Virus Infection, Annu. Rev. Phytopathol. 1990, 28:451-74. Copyright 1990 by Annual Reviews Inc. 0066-4286/90/0901-0451$02.00.
Thomas W. Becker, et al., The cab-m7 gene: a light-inducible, mesophyll-specific gene of maize, accepted in revised form Apr. 16, 1992, Plant Moleuclar Biology 20: 49-60, 1992. Copyright 1992 Kluwer Academic Publishers. Printed in Belgium.
R. Bernardo, et al., North American study or essential derivation in maize: inbreds developed without and with selection from F2 populations, Accepted: Jul. 28, 2000, Theor Appl Genet (2001) 102:986-992. Copyright Springer-Verlag 2001.

Jose R. Botella, et al., Differential expression of two calmodulin genes in response to physical and chemical stimuli, accepted in revised form Jan. 12, 1994. Plant Molecular Biology 24: 757-766, 1994. Copyright 1994 Kluwer Academic Publishers. Printed in Belgium.
Steven P. Briggs, Plant Disease Resistance, Grand unification theory in sight, Molecular characterization of the components of signalling pathways that mediate disease resistance is at least providing a unified picture of how plants fight disease. Copyright Current Biology 1995, vol. 5, No. 2., pp. 128-131.
Rachel A. Burton, et al., Virus-Induced Silencing of a Plant Cellulose Synthase Gene, The Plant Cell, vol. 12, 691-705, May 2000. www.plantcell.org Copyright 2000 American Society of Plant Physiologists. Copyright American Society of Plant Biologists. Advancing the Science of Plant Biology.
W. R. Busnell, et al., Genetic engineering of disease resistance in cereals, , The Canadian Phytopathological Society, vol. 20(2):137-220 Jun. 1998, ISSN 0706-0661. Accepted for publication Mar. 30, 1998. This paper was presented at a symposium on bioengineering plants for disease resistance, held at the annual meeting of the Canadian Phytopathological Society, Jul. 6-9, 1997. Canadian Journal of Plant Pathology, Online publication date: Dec. 22, 2009. To link to this Article: DOI: 10.1080/07060669809500419. Publisher Taylor & Francis.
Martin Chalfie, et al., Green Fluorescent Protein as a Marker for Gene Expression, Source: Science, New Series, vol. 263, No. 5148 (Feb. 11, 1994), pp. 802-803. Published by: American Association for the Advancement of Science. Stable URL: http://www.jstor.org/stable/2882924 Accessed: Apr. 24, 2008 19:27.
S. T. Chalyk, et al., Transgressive segregation in the progeny of a cross between two inducers of maize maternal haploids, Maize Genetics Cooperation News Letter (Journal Article), Std. No. 10904573, Issue 68, p. 47, Pub Date: 1994.
Pierre J. Charest, et al., In vitro study of transgenic tobacco expressing *Arabidopsis* wild type and mutant acetohydroxyacid synthase genes. Communicated by F. Constabel. Plant Cell Reports (1990) 8: 643-646. Copyright Springer-Verlag 1990.
Cho, Un-Haing, et al., Detection of Genetic Variation and Gene Introgression in Potato Dihaploids Using Randonly Amplified Polymorphic DNA (RAPD) Markers, J. Plant Biol. 39(3): 185-188 (1996). Copyright 1996 by Botanical Society of Korea, Seoul.
Alan H. Christensen, et al., Sequence analysis and transcriptional regulation by heat shock of polyubiquitin transcripts from maize. accepted in revised form Feb. 7, 1989. Plant Molecular Biology 12: 619-632, 1989. Copyright 1989 Kluwer Academic Publishers. Printed in Belgium.
Alan H. Christensen, et al., Maize polyubiquitin genes: structure, thermal perturbation of expression and transcript splicing, and promoter activity following transfer to protoplasts by electroporation. accepted in revised form Oct. 25, 1991. Plant Molecular Biology 18: 675-689, 1992. Copyright 1992 Kluwer Academic Publishers. Printed in Belgium.
Paul Christou, et al., Stable transformation of soybean by electroporation and root formation from transformed callus. Communicated by Oliver E. Nelson, Jr., Feb. 25, 1987. Proc. Natl. Acad. Sci. USA, vol. 84, pp. 3962-3966, Jun. 1987. Applied Biology.
Phan V. Chuong, et al., A simple culture method for *Brassica hypototyl* protoplasts. Communicated by F. Constabel. Plant Cell Reports (1985) 4:4-6.
L. Comai, et al., Expression in plants of a mutuant aroA gene from *Salmonella typhimurium* confers tolerance to glyphosate. Letters to Nature, Nature vol. 317 Oct. 24, 1985, pp. 741-744. Copyright 1985 Nature Publishing Group.
Ben J. C. Cornelissen, et al., Update on Biotechnology, Strategies for Control of Fungal Diseases with Transgenic Plants, Plant Physiol. (1993) 101: 709-712.
Gary Creissen, et al., Short Communication, Molecular characterization of gluthathione reductase cDNAs from pea (*Pisum stavum* L.). The Plant Journal (1991) 2(1), 129-131.
Swapan K. Datta, et al., Herbicide-resistant *Indica* rice plants from IRRI breeding line IR72 after PEG-mediated transformation of

(56) References Cited

OTHER PUBLICATIONS protoplasts. accepted in revised form Jun. 8, 1992. Plant Molecular Biology 20: 619-629, 1992. Copyright 1992 Kluwer Academic Publishers. Printed in Belgium.

Marc De Block, et al., Expression of foreign genes in regenerated plants and in their progeny. The EMBO Journal vol. 3 No. 8 pp. 1681-1689, 1984. Copyright IRL Press Limited, Oxford, England.

Willy De Greef, et al., Evaluation of Herbicide Resistance in Transgenic Crops Under Field Conditions, Bio/Technology vol. 7 Jan. 1989, pp. 61-64. Copyright 1989 Nature Publishing Group http://www.nature.com/naturebiotechnology.

Alain Deshayes, et al., Liposome-mediated transformation of tobacco mesophyll protoplasts by an *Escherichia coli* plasmid, The EMBO Journal vol. 4 No. 11 pp. 2731-2737, 1985. Copyright IRL Press Limited, Oxford, England.

Kathleen D'Halluin, et al., Transgenic Maize Plants by Tissue Electroporation, The Plant Cell, vol. 4, 1495-1505, Dec. 1992. Copyright 1992 American Society of Plant Physiologists.

J. Draper, et al., Ti Plasmid Homologous Sequences Present in Tissues from *Agrobacterium* Plasmid-transformed *Petunia* Protoplasts, Plant & Cell Physiol. 23(3): 451-458 (1982).

David A. Eichholtz, et al., Expression of Mouse Dihydrofolate Reductase Gene Confers Methotrexate Resistance in Transgenic *Petunia* Plants. Final Oct. 6, 1986. Somatic Cell and Molecular Genetics, vol. 13, No. 1, 1987, pp. 67-76. 0740-7750/87/0100-006$05.00/0 Copyright 1987 Plenum Publishing Corporation.

Kathryn J. Elliott, et al., Isolation and characterization of fruit vacuolar invertase genes from two tomato species and temporal differences in mRNA levels during fruit ripening. accepted in revised form Oct. 20, 1992. Plant Molecular Biology 21: 515-524, 1993. Copyright 1993 Kluwer Academic Publishers. Printed in Belgium.

Jean Finnegan, et al., Transgene Inactivation: Plants Fight Back!, Review, Bio/Technology vol. 12 Sep. 1994, pp. 883-888. Copyright 1994 Nature Publishing Group http://www.nature.com/aturebiotechnology.

Dane K. Fisher, et al., Plant Gene Register, Starch Branching Enzyme II from Maize Endosperm, Plant Physiol. (1993) 102: 1045-1046.

R. B. Flavell, Review, Inactivation of gene expression in plants as a consequence of specific sequence duplication, Pro. Natl. Acad. Sci. USA, vol. 91, pp. 3490-3496, Apr. 1994.

Elizabeth B. P. Fontes, et al., Characterization of an Immunoglobulin Binding Protein Homolog in the Maize flourly-2 Endosperm Mutant, The Plant Cell. vol. 3, 483-496, May 1991. Copyright 1991 American Society of Plant Physiologists.

Robert T. Fraley, et al., Expression of bacterial genes in plant cells, Proc. Natl. Acad. Sci. USA, vol. 80, pp. 4803-4807, Aug. 1983. Genetics.

Christiane Gatz, et al., Regulation of a modified CaMV 35S promoter by the Tn10-encloded Tet repressor in transgenic tobacco, Mol. Gen. Genet (1991) 227:229-237. 002689259100168M.

Frank T. Roder, et al., Efficiency of the tetracycline-dependent gene expression system: complete suppression and efficient induction of the rolB phenotype in transgenic plants. Accepted: Oct. 11, 1993. Mol. Gen. Genet. (1994) 243:32-38. Copyright Springer-Verlag 1994.

William J. Gordon-Kamm, et al., Transformation of Maize Cells and Regeneration of Fertile Transgenic Plants. The Plant Cell, vol. 2, 603-618, Jul. 1990. Copyright 1990 American Society of Plant Physiologists.

Stephen J. Gould, et al., A Conserved Tripeptide Sorts Priteins to Peroxisomes, Published May 1, 1989, The Journal of Cell Biology, vol. 108, May 1989 1657-1664. Copyright The Rockefeller University Press, 0021-9525/89/05/1657/8 $2.00.

Eike A. Griess, et al., Plant Gene Register, Plant Physiol. (1994) 104: 1467-1468.

Margaret Y. Gruber, et al., Chapter 7, Vectors for Plant Transformation, Methods in Plant Molecular Biology and Biotechnology, Std. No. 9780849351648, pp. 89-119, Published 1993.

Bernard R. Glick, et al., References, Methods in plant molecular biology and biotechnology, Std. No. 9780849351648, pp. 284-285, Published 1993.

Felix D. Guerrero, et al., Promoter sequences from a maize pollen-specific gene direct tissue-specific transcription in tobacco, Mol. Gen. Genet. (1990) 24: 161-168. Copyright Springer-Verlag 1990.

R. Hain, et al., Uptake, integration, expression and genetic transmission of a selectable chimaeric gene by plant protoplasts, Mol. Gen. Genet. (1985) 199: 161-168. Copyright Springer-Verlag 1985.

Bruce D. Hammock, et al., Expression and effects of the juvenile hormone esterase in a baculovirus vector, Letters to Nature, Nature, vol. 344, pp. 485-461, Mar. 29, 1990.

Jim Haseloff, et al., Article, Simple RNA enzymes with new and highly specific endoribonuclease activities, Nature vol. 334, pp. 585-591, Aug. 18, 1988. Copyright 1988 Nature Publishing Group.

Jiro Hattori, et al., Original Paper, An acetohydroxy acid synthase mutant reveals a single site involved in multiple herbicide resistance, Accepted Aug. 18, 1994, Mol. Gen. Genet (1995) 246: 419-425. Copyright Springer-Verlag 1995.

John D. Hayes, et al., Molecular cloning and heterologous expression of a cDNA encoding a mouse glutathione S-transferase Yc subunit possessing high catalytic activity for aflatoxin B1-8,9-epoxide, Biochem. J. (1992) 285, 173-180 (Printed in Great Britain).

Maria B. Hayford, et al., Development of a Plant Transformation Selection System Based on Expression of Genes Encoding Gentamicin Acetyltransferases, and in revised form Jan. 8, 1988. Plant Physiol. 86, 1216-1222. 0032-0889/88/86/126/07/$01.00/0.

Gayle Heney, et al., The Purification of Avidin and Its Derivatives on 2-Iminobiotin-6aminohexyl-Sepharose 4B, Analytical Biochemistry 114, 92-96 (1981). 0003-2697/81/090092-05$02.00/0. Copyright 1981 by Academic Press, Inc.

Christiane Gatz, et al., Regulation of a modified CaMV 35S promoter by the TN10-encoded Tet represssor in transgenic tobacco, Mol. Gen. Genet (1991) 227: 229-237. 00268925100168M.

Jacques Hille, et al., Bleomycin resistance: a new dominant selectable marker for plant cell transformation, Plant Molecular Biology 7: 171-176 (1986). Copyright Martinus Nijhoff Publishers, Dordrecht—Printed in Netherlands.

Canadian Intellectual Property Office, Official Action issued Jul. 16, 2012, Canadian Patent Application No. 2,696,355 filed Mar. 10, 2010, Applicant Monsanto Technology LLC.

Canadian Intellectual Property Office, Official Action issued Jul. 16, 2012, Canadian Patent Application No. 2,696,166 filed Mar. 10, 2010, Applicant Monsanto Technology LLC.

Canadian Intellectual Property Office, Official Action issued Jul. 18, 2012, Canadian Patent Application No. 2,696,162 filed Mar. 10, 2010, Applicant Monsanto Technology LLC.

Neff, W.E. et at., Journal of the American Oil Chemists' Society, 71/10, pp. 1101-1109, Oct. 1994 (abstract).

Canadian Office Action dated Aug. 29, 2013 for Canadian Patent Application No. 2,696,166.

Canadian Office Action dated Aug. 27, 2013 for Canadian Patent Application No. 2,669,444.

Canadian Office Action dated Aug. 22, 2013 for Canadian Patent Application No. 2,706,945.

Canadian Office Action dated Aug. 29, 2013 for Canadian Patent Application No. 2,696,162.

Canadian Intellectual Property Office, Official Action issued May 15, 2012, Canadian Patent Application No. 2,665,608, filed May 7, 2009, Applicant Monsanto Technology LLC.

Canadian Intellectual Property Office, Official Action issued May 17, 2012, Canadian Patent Application No. 2,665,613, filed May 7, 2009, Applicant Monsanto Technology LLC.

Canadian Intellectual Property Office, Official Action issued May 23, 2012, Canadian Patent Application No. 2,665,606, filed May 7, 2009, Applicant Monsanto Technology LLC.

U.S. Patent and Trademark Office, Non-Final Office Action, mailed Jul. 1, 2011, U.S. Appl. No. 12/486,161, filed Jun. 17, 2009, Confirmation No. 4613, Zenon Lisieczko.

Grahame E. Pratt, et al., Identification of an Allatostatin from Adult *Diploptera punctata*, Biochemical and Biophysical Research Communications, vol. 163, No. 3, 1989, Sep. 19, 1989, pp. 1243-1247.

(56) References Cited

OTHER PUBLICATIONS 0006-291X/89 $.50. Copyright 1989 by Academic Press, Inc. All rights of reproduction in any form reserved.

Elisabeth Przibilla, et al., Site-Specific Mutagenesis of the D1 Subunit of Photosystem II in Wild-Type Chlamydomonas, accepted Nov. 16, 1990, The Plant Cell, vol. 3, 169-174, Feb. 1991. Copyright 1991 American Society of Plant Physiologists.

V. Raboy, et al., A survey of maize kernel mutants for variation in phytic acid, Maydica 35 (1990): 383-390.

John C. Sanford, et al., Delivery of Substances into Cells and Tissues Using a Particle Bombardment Process, Particulate Science and Technology 5:27-37, 1987. Copyright 1987 by Hemisphere Publishing Corporation.

John C. Sanford, Biolistic plant transformation, revised Oct. 18, 1989, Physiologia Plantarum 79: 206-209. Copenhagen 1990.

John C. Sanford, Reviews, The biolistic process, TIBTECH, Dec. 1988 [vol. 6], pp. 299-302, Copyright 1988, Elsevier Science Publishers Ltd. (UK) 0167-9430/88/$02.00.

Mark Schena, et al., A steroid-inducible gene expression system for plant cells, Contributed by Ronald W. Davis, Aug. 8, 1991, Proc. Natl. Acad. Sci. USA, vol. 88, pp. 10421-10425, Dec. 1991, Genetics.

Champa Sengupta-Gopalan, et al., Developmentally regulated expression of the bean B-phaseolin gene in tobacco seed, Communicated by Arthur Kelman, Jan. 14, 1985, Proc. Natl. Acad. Sci. USA, vol. 82, pp. 3320-3324, May 1985, Developmental Biology.

Dilip M. Shah, et al., Engineering Herbicide Tolerance in Transgenic Plants, Science, vol. 233, pp. 478-481, Dec. 12, 1985; accepted May 6, 1986.

Phillip A. Sharp, RNAi and double-strand RNA, Genes Dev. 1999 13: 139-141 Cold Spring Harbor Laboratory Press. To subscribe to Genes & Development go to: http://genesdev.cshlp.org/subscriptions.

Raymond E. Sheehy, et al., Reduction of polygalacturonase activity in tomato fruit by antisense RNA, Communicated by E. Peter Geiduschek, Aug. 4, 1988, Proc. Natl., Acad. Sci. USA, vol. 85, pp. 8805-8809, Dec. 1988, Biochemistry.

Teruaki Shiroza, et al., Sequence Analysis of the *Streptococcus mutans* Fructosyltransferase Gene and Flanking Regions, Accepted Nov. 19, 1987, Journal of Bacteriology, Feb. 1988, p. 810-816. 0021-9193/88/020810-07$02.00/0. Copyright 1988, American Society for Microbiology.

June Simpson, et al., Light-inducible and tissue-specific expression of a chimaeric gene under control of the 5'-flanking sequence of a pea chlorophyll a/b-binding protein gene, The EMBO Journal, vol. 4, No. 11, pp. 2723-2729, 1985. Copyright IRL Press Limited, Oxford, England.

Neil A. Smith, et al., Gene expression, Total silencing by intron-spliced hairpin RNAs, Nature, vol. 407, Sep. 21, 2000, pp. 319-320, www.nature.com Copyright Macmillan Magazines Ltd.

Morten Sogaardt, et al., Site-directed Mutagenesis of Histidine 93, Aspartic Acid 180, Glutamic Acid 205, Histidine 290, and Aspartic Acid 291 at the Active Site and Tryptophan 279 at the Raw Starch Binding in Barley α-Amylase 1, (and in revised form, May 14, 1993) The Journal of Biological Chemistry, vol. 268, No. 30, Issue of Oct. 25, pp. 22480-22484, 1993, Copyright 1993 by The American Society for Biochemistry and Molecular Biology, Inc. Printed in U.S.A.

Imre E. Somssich, Previews, Closing Another Gap in the Plant SAR Puzzle, Cell, 2003, pp. 815-816.

Cheryl Montain Laursen, et al., Production of fertile transgenic maize by electroporation of suspension culture cells, accepted in revised form Sep. 17, 1994, Plant Molecular Biology 24: 51-61, 1994. Copyright 1994 Kluwer Academic Publishers. Printed in Belgium.

David M. Stalker, et al., Herbicide Resistance in Transgenic Plants Expressing a Bacterial Detoxification Gene, Apr. 29, 1988; accepted Aug. 9, 1988, Reports, Oct. 21, 1988, pp. 419-423.

Virginia Stiefel, et al., Expression of a Maize Cell Wall Hydroxyproline-Rich Glycoprotein Gene in Early Leaf and Root Vascular Differentiation, revised Jun. 8, 1990, The Plant Cell, vol. 2, 785-793, Aug. 1990. Copyright 1990 American Society of Plant Physiologists.

Peter Steinecke, et al., Expression of a chimeric ribozyme gene results in endonucleolytic cleavage of target mRNA and a concomitant reduction of gene expression in vivo, revised on Dec. 20, 1991, The EMBO Journal, vol. 11, No. 4, pp. 1525-1530, 1992. Copyright Oxford University Press.

Michel Steinmetz, et al., The DNA sequence of the gene for the secreted *Bacillus subtilis* enzyme levansucrase and its genetic control sites, Mar. 18, 1985, Mol. Gen. Genet (1985) 200: 220-228. Copyright Springer-Verlag 1985.

Jun-Ichi Sumitani, et al., Molecular Cloning and Expression of Proteinaceous α-Amylase Inhibitor Gene from *Streptomyces nitrosporeus* in *Escherichia coli*, Biosci. Biotech. Biochem., 57 (8), 1243-1248, 1993.

Zora Svab, et al., Aminoglycoside-3"-denyltransferase confers resistance to spectinomycin and streptomycin in *Nicotiana tabacum*, accepted Sep. 19, 1989, Plant Molecular Biology 14: 197-205, 1990. Copyright 1990 Kluwer Academic Publishers. Printed in Belgium.

Paraskevi Taviadoraki, et al., Transgenic plants expressing a functional single-chain Fv antibody are specifcally protected from virus attack, Letters to Nature, Nature, vol. 366, Dec. 2, 1993, pp. 469-472. Copyright 1993 Nature Publishing Group.

Crispin B. Taylor, In this issue: Comprehending Cosuppression, The Plant Cell, vol. 9, 1245-1249, Aug. 1997.

T.H. Teeri, et al., Gene fusions to lacZ reveal new expression patterns of chimeric genes in transgenic plants, revised on Dec. 2, 1988, The EMBO Journal, vol. 8, No. 2, pp. 343-350, 1989. Copyright IRL Press.

M. P. Timko, et al., Letters to Nature, Light regulation of plant gene expression by an upstream enhancer-like element, accepted Oct. 9, 1985, Nature, vol. 318, Dec. 12, 1985, pp. 579-582. Copyright 1985 Nature Publishing Group.

Patrick Toubart, et al., Cloning and characterization of the gene encoding the endopolygalacturonase-inhibiting protein (PGIP) of *Phaseolus vulgaris* L., revised Jan. 2, 1992, The Plant Journal (1992) 2(3), 367-373.

Kazuhiro Toyoda, et al., Review: Resistance and susceptibility of plants to fungal pathogens, Transgenic Research 11: 567-582, 202. Copyright 2002 Kluwer Academic Publishers. Printed in the Netherlands.

David Twell, et al., Isolation and expression of an anther-specific gene from tomato, Mol. Gen. Genet (1989) 217: 240-245. Copyright Springer-Verlag 1989.

David Twell, et al., Activation and developmental regulation of an *Arabidopsis* anther-specific promoter in microspores and pollen of *Nicotiana tabacum*, Sexual Plant Reproduction (1993), 6: 217-224. Copyright Springer-Verlag 1993.

Els J. M. Van Damme, et al., Short Communication: Molecular cloning of mannose-binding lectins from *Clivia miniata*, accepted in revised form Jan. 24, 1994, Plant Molecular Biology 24: 825-830, 1994. Copyright 1994 Kluwer Academic Publishers. Printed in Belgium.

Wim Van Hartingsveldt, et al., Gene 07019, Cloning, characterization and overexpression of the phytase-encoding encoding gene (phyA) of *Aspergillus niger*, Revised/Accepted: Dec. 10/Dec. 12, 1992; Gene, 127 (1993) 87-94. Copyright 1993 Elsevier Science Publishers B.V. All rights reserved. 0378-1119/93/$06.00.

Peter J. M. Van Den Elzen, et al., Short Communication: A chimaeric hygromycin resistance gene as a selectable marker in plant cells, in revised form Jul. 17, 1985; accepted Jul. 27, 1985, Plant Molecular Biology 5: 299-302, 1985. Copyright Martinus Nijhoff Publishers, Dordrecht—Printed in The Netherlands.

L. Verdoodt, et al., Use of the multi-allelic self-incompatibility gene in apple to assess homozygocity in shoots obtained through haploid induction, Accepted: Sep. 10, 1997, Theor Appl Genet (1998) 96: 294-300. Copyright Springer-Verlag 1998.

Vicki Chandler, Chapter 118, Overview of Cloning Genes Using Transposon Tagging, The Maize Handbook—M. Freeling, V. Walbott, eds., pp. 647-652. Copyright 1994 Springer-Verlag, New York, Inc. Supplied by the British Library—"The world's knowledge".

(56) References Cited

OTHER PUBLICATIONS

Y. Wan, et al., Efficient production of doubled haploid plants through colchicine treatment of anther-derived *Maize callus*, Accepted Nov. 28, 1988, Theor Appl Genet (1989) 77: 889-892, Copyright Springer-Verlag 1989.
David G. Wang, et al., Reports, Large-Scale Identification, Mapping, and Genotyping of Single-Nucleotide Polymorphisms in the Human Genome, Feb. 5, 1998; accepted Mar. 31, 1998, Science, vol. 280, May 15, 1998, pp. 1077-1082. www.sciencemag.org.
E. R. Ward, et al., Update section, Mini review, Chemical regulation of transgene expression in plants, Plant Molecular Biology 22: 361-366, 1993. Copyright 1993 Kluwer Academic Publishers. Printed in Belgium.
Phillip D. Zamore, et al., RNAi: Double-Stranded RNA Directs the ATP-Dependent Cleavage of mRNA at 21 to 223 Nucleotide Intervals, Cell, vol. 101, 25-33, Mar. 31, 2000. Copyright 2000 by Cell Press.
Li-Jian Zhang, et al.,, Efficient Transformation of Tobacco by Ultrasonication, accepted Jun. 14, 1991, Copyright 1991 Nature Publishing Group. http://www.nature.com/naturebiotechnology.
R. B. Horsch, et al., A Simple and General Method for Transferring Genes into Plants, Mar. 8, 1985, pp. 1229-1231.
Huub J.M. Linthorst, et al., Tobacco proteinase inhibitor I genes are locally, but not systemically induced by stress, accepted in revised form Dec. 20, 1992. Plant Molecular Biology 21:985-992, 1993. Copyright 1993 Kluwer Academic Publishers. Printed in Belgium.
Jesse M. Jaynes, et al., Expression of a Cecropin B lytic peptide analog in transgenic tobacco confers enhanced resistance to bacterial wilt caused by *Pseudomonas solanacearum*, accepted Dec. 7, 1992). 0168-9452/93$06.00 Copyright 1993 Elsevier Scientific Publishers Ireland Ltd. Printed and Published in Ireland.
Richard A. Jefferson, Experimental Protocols, Assaying Chimeric Genes in Plants: The GUS Gene Fusion System, Plant Molecular Biology Reporter, vol. 5, No. 1, 1987, pp. 387-405.
Jonathan D.G. Jones, et al., A dominant nuclear streptomycin resistance marker for plant cell transformation, Mol. Gen. Genet. (1987) 210: 86-91. Copyright Springer-Verlag 1987.
David A. Jones, et al., Reports, Isolation of the Tomato Cf-9 Gene for Resistance to *Cladosporium fulvum* by Transposon Tagging, Science, vol. 266, pp. 789-793, Nov. 4, 1994.
Richard Jorgensen, Undercurrents, Altered gene expression in plants due to trans interactions between homologous genes, TIBTECH—Dec. 1990 (vol. 8) pp. 340-344. Copyright 1990, Elsevier Science Publishers Ltd. (UK) 0167-940/90/$2.00.
Clarence I. Kado, Ph.D., Molecular Mechanisms of Crown Gall Tumorigenesis, Critical Reviews in Plant Sciences, 10(1):1-32 (1991). 0735-2689/91/$.50 Copyright 1991 by CRC Press, Inc.
Daniel Kalderon, et al., A Short Amino Acid Sequence Able to Specify Nuclear Location, Cell, vol. 39, 499-509, Dec. 1984 (Part 2), Copyright 1984 by MT. 0092-8674/84/130499-11 $02.00/0.
K. K. Kartha, et al., In vitro Plant Formation from Stem Explants of Rape (*Brassica napus* cv. Zephyr), Physiol. Plant. 31: 217-220, 1974.
Petra Kawalleck, et al., Polyubiquitin gene expression and structural properties of the ubi4-2 gene in *Petroselinum crispum*, accepted in revised form Nov. 22, 1992, Plant Molecular Biology 21: 673-684, 1993. Copyright 1993 Kluwer Academic Publishers. Printed in Belgium.
T. M. Klein, Factors Influencing Gene Delivery Into *Zea mays* Cells by High-Velocity Microprojectiles, Bio/Technology vol. 6, May 1988, pp. 559-563. Copyright 1988 Nature Publishing Group http://www.nature.com/naturebiotechnology.
Cheryl A. P. Knox, et al., Structure and organization of two divergent α-amylase genes from barley, in revised form Mar. 2, 1987; accepted Mar. 3, 1987, Plant Molecular Biology 9: 3-17 (1987). Copyright Martinus Nijhoff Publishers, Dordrecht—Printed in the Netherlands.
Deborah S. Knutzon, et al., Modification of *Brassica* seed oil by antisense expression of a stearoyl-acyl carrier protein desaturase gene, Communicated by Donald R. Helinski, Dec. 23, 1991, Proc. Natl. Acad. Sci. USA, vol. 89, pp. 2624-2628, Apr. 1992. Plant Biology.

Mitsue Kobayashi, et al. Haploid induction and its genetic mechansim in alloplasmic common wheat, The Journal of Heredity 71: 9-14, 1980.
Csaba Koncz, et al., Expression and assembly of functional bacterial luciferase in plants, Contributed by Jeff Schell, Sep. 10, 1986, Proc. Natl. Acad. Sci. USA, vol. 84, pp. 131-135, Jan. 1987, Cell Biology.
Karl J. Kramer, et al., Sequence of a cDNA and Expression of the Gene Encoding Epidermal and Gut Chitinases of *Manduca sexta*, revised and accepted Jan. 13, 1993. Insect Biochem. Molec. Biol. vol. 23, No. 6, pp. 691-701, 1993. Printed in Great Britain. 0965-1748/93 $6.00 + 0.00, Pergamon Press Ltd.
Christopher J. Lamb, et al., Review/Emerging Strategies for Enhancing Crop Resistance to Microbial Pathogens, Biotechnology vol. 10, Nov. 1992, pp. 1436-1445. Copyright 1992 Nature Publishing Group http://www.nature.com/naturebiotechnology.
Corne MJ Pieterse, et al., NPR1: the spider in the web of induced resistance signaling pathways, Current Opinion in Plant Biology 2004, 7:456-464. Elsevier. Full text provided by www.sciencedirect.com.
Joan T. Odell, et al., Letters to Nature, Identification of DNA sequences required for activity of the cauliflower mosaic virus 35S promoter, Nature vol. 313, Feb. 28, 1985. Copyright 1985 Nature Publishing Group.
S. B. Narasimhulu, et al., Species specific shoot regeneration response of cotyledonary explants of *Brassicas*, Communicated by E. Earle, Plant Cell Reports (988) 7: 104-106. Plant Cell Reports Copyright Springer-Verlag 1988.
Wyatt Paul, et al., The isolation and characterization of the tapetum-specific *Arabidopsis thaliana* A9 gene, accepted in revised form Mar. 19, 1992, Plant Molecular Biology 19: 611-622, 1992. Copyright 1992 Kluwer Academic Publishers. Printed in Belgium.
Jan Van Parijs, et al., Hevein: an antifungal protein from rubber-tree (*Hevea brasiliensis*) latex, accepted Jul. 25, 1990, Planta (1991) 183: 258-264. Planta Copyright Springer-Verlag 1991.
F. Neuhuber, et al., Susceptibility of transgene loci to homology-dependent gene silencing, Accepted: Feb. 7, 1994, Mol. Gen. Genet (1994) 244: 230-241. Copyright Springer-Verlag 1994.
D. I. Last, et al., pEmu: an improved promoter for gene expression in cereal cells, Accepted Oct. 16, 1990, Theor. Appl. Genet (1991) 81: 581-588.
Kathleen Y. Lee, et al., The molecular basis of sulfonylurea herbicide resistance in tobacco, The EMBO Journal vol. 7, No. 5, pp. 1241-1248, 1988.
Marc Lepetit, et al., A plant histone gene promoter can direct both replication-dependent and -independent gene expression in transgenic plants, Mol. Gen. Genet (1992) 231: 276-285, MGG Copyright Springer-Verlag 1992.
David R. Lerner, et al., Cloning and Characterization of Root-Specific Barley Lectin, and in revised form May 3, 1989, Plant Physiol. (1989) 91, 124-129, 0032-0889/89/91/0124/06/$01.00/0.
J. Logemann, et al., Expression of a Barley Ribosome-Inactivating Protein Leads to Increased Fungal Protection in Transgenic Tobacco Plants, Bio/Technology, vol. 10, Mar. 1992, pp. 305-308. Copyright 1992 Nature Publishing Group http://www.nature.com/naturebiotechnology.
L.A. Lyznik, et al., Site-specific recombination for genetic engineering in plants, Revised: Feb. 19, 2003 / Accepted: Feb. 24, 2003 / Published online: Apr. 26, 2003. Plant Cell Rep (2003) 21: 925-932. DOI 10.1007/s00299-003-0616-7. Copyright Springer-Verlag 2003.
L. C. Marshall, et al., Allelic mutations in acetyl-coenzyme A carboxylase confer herbicide tolerance in maize, Accepted Jul. 9, 1991, Theor. Appl. Genet (1992) 83: 435-442. Copyright Springer-Verlag 1992.
Gregory B. Martin, et al., Reports, Map-Based Cloning of a Protein Kinase Gene Conferring Disease Resistance in Tomato, Science, vol. 262, pp. 1432-1436, Nov. 26, 1993.
J. Velten, et al., Isolation of a dual plant promoter fragment from the Ti plasmid of *Agrobacterium tumefaciens*, The EMBO Journal, vol. 3, No. 12, pp. 2723-2730, 1984. Copyright IRL Press Limited, Oxford, England.

(56) References Cited

OTHER PUBLICATIONS

Ken Matsuoka, et al., Propeptide of a precursor to a plant vacuolar protein required for vacuolar targeting, Communicated by Shang Fa Yang, Oct. 15, 1990, Proc. Natl. Acad. Sci. USA, vol. 88, pp. 834-838, Feb. 1991, Cell Biology.

John M. McDowell, et al., Review, Plant disease resistance genes: recent insights and potential applications, Trends in Biotechnology, vol. 21, No. 4, pp. 178-183, Apr. 2003. http://tibtec.trends.com 0167-7799/01/$—see front matter. Copyright 2003 Elsevier Science Ltd. All rights reserved. doi:10.1016/S0167-7799(03)00053-2.

David McElroy, et al., Isolation of an Efficient Actin Promoter for Use in Rice Transformation, The Plant Cell, vol. 2, 163-171, Feb. 1990. Copyright 1990 American Society of Plant Physiologist.

Vadim L. Mett, et al., Copper-controllable gene expression system for whole plants, Communicated by Eric E. Conn, Jan. 26, 1993, Proc. Natl. Acad. Sci. USA, vol. 90, pp. 4567-4571, May 1993, Plant Biology.

B. L. Miki, et al., Methods in Plant Molecular Biology and Biotechnology, Chapter 6, Procedures for Introducing Foreign DNA into Plants, pp. 67-88. 0-8493-5164-2/93/$0.00+$.50. Copyright 1993 by CRC Press, Inc.

B. L. Miki, et al., Transformation of *Brassica napus* canola cultivars with *Arabidopsis thaliana* acetohydroxyacid synthase genes and analysis of herbicide resistance, Accepted Apr. 11, 1990, Theor. Appl. Genet (1990) 80: 449-458. Copyright Springer-Verlag 1990.

Michael Mindrinos, et al., The *A. thaliana* Disease Resistance Gene RPS2 Encodes a Protein Containing a Nucleotide-Binding Site and Leucine-Rich Repeats, *Arabidopsis* Disease Resistance Gene, Cell, vol. 78, 1089-1099, Sep. 23, 1994, Copyright 1994 by Cell Press.

Maurice M. Moloney, et al., High efficiency transformation of *Brassica napus* using *Agrobacterium* vectors, Communicated by F.Constable, Plant Cell Reports (1989) 8:238-242. Copyright Springer-Verlag 1989.

Mary K. Montgomery, et al., RNA as a target of double-stranded RNA-mediated genetic interference in *Caenorhabditis elegans*, Communicated by Joseph G. Gall, . . . , Nov. 2, 1998, Proc. Natl. Acad. Sci. USA, vol. 95, pp. 15502-15507, Dec. 1998. Genetics. Copyright 1998 by the National Academy of Sciences 0027-8424/98/9515502-6$2.00/0 PNAS is available online at www.pnas.org.

Norimoto Murai, et al., Research Article, Phaseolin Gene from Bean Is Expressed After Transfer to Sunflower Via Tumor-Inducing Plasmid Vectors, Science, vol. 222, pp. 476-482. accepted Sep. 14, 1983.

Carolyn Napoli, et al., Introduction of a Chimeric Chalcone Synthase Gene into Petunia Results in Reversible Co-Suppression of Homologous Genes in trans, The Plant Cell, vol. 2, 279-289, Apr. 1990, Copyright 1990 American Society of Plant Physiologists.

S.J. Openshaw, et al., Marker-assisted Selection in Backcross Breeding, Analysis of Molecular Marker Data, Joint Plant Breeding Symposia Series, Aug. 5-6, 1994, Corvallis, Oregon, American Society for Horticultural Science Crop Science Society of America, pp. 41-43. Supplied by The British Library—"The world's knowledge".

Sheng-Zhi Pang, et al., Expression of a gene encoding a scorpion insectotoxin peptide in yeast, bacteria and plants, Gene. 116 (1992) 165-172, Copyright 1992 Elsevier Science Publishers B.V. All rights reserved 0378-119/92/$05.00.

Jan Pen, et al., Research, Production of Active *Bacillus licheniformis* Alpha-Amylase in Tobacco and Its Application in Starch Liquefaction, Bio/Technology, vol. 10, pp. 292-296, Mar. 1992. Copyright 1992 Nature Publishing Group http://www.nature.com/naturebiotechnology.

Rhonda Perriman, et al., A Ribozyme That Enhances Gene Suppression in Tobacco Protoplasts, accepted for publication Jun. 2, 1993, Antisense Research and Development, 3:253-263 (1993) Mary Ann Liebert, Inc., Publishers.

J. Plieske, et al., Microsatellite markers for genome analysis in *Brassica*. I. development in *Brassica napus* and abundance in *Brassicaceae* species, Theor Appl. Genet (2001) 102: 689-694. Copyright Springer-Verlag 2001.

M. Pollacsek, Plant improvement, Management of the ig gene for haploid induction in maize, (accepted Jan. 16, 1992), Agronomie (1991) 12, 247-251. Copyright Elsevier/INRA.

United States Patent and Trademark Office, Non-Final Office Action, mailed Dec. 29, 2011, U.S. Appl. No. 12/713,411, filed Feb. 26, 2010, Jun Liu.

United States Patent and Trademark Office, Non-Final Office Action, mailed Dec. 29, 2011, U.S. Appl. No. 12/713,479, filed Feb. 26, 2010, Jun Liu.

United States Patent and Trademark Office, Non-Final Office Action, mailed Dec. 29, 2011, U.S. Appl. No. 12/713,594, filed Feb. 26, 2010, Dale Burns.

United States Patent and Trademark Office, Non-Final Office Action, mailed Dec. 29, 2011, U.S. Appl. No. 12/721,637, filed Mar. 11, 2010, Chunren Wu.

\* cited by examiner

PLANTS AND SEEDS OF SPRING CANOLA VARIETY SCV425044

BACKGROUND OF THE INVENTION

1. Field of the Invention

The present invention relates to a new and distinctive canola line, designated SCV425044. All publications cited in this application are herein incorporated by reference.

2. Description of Related Art

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of canola plant breeding is to develop new, unique and superior canola cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same canola traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable because the breeder's selection occurs in unique environments, with no control at the DNA level (using conventional breeding procedures), and with millions of different possible genetic combinations being generated.

A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new canola cultivars.

The development of new canola lines requires the development and selection of canola varieties, the crossing of these varieties and selection of superior hybrid crosses. The hybrid seed is produced by manual crosses between selected male-fertile parents or by using male sterility systems. These hybrids are selected for certain single gene traits such as flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Canola, *Brassica napus oleifera annua*, is an important and valuable field crop. Thus, a continuing goal of canola plant breeders is to develop stable, high yielding canola lines that are agronomically sound. The reasons for this goal are obviously to maximize the amount of grain produced on the land used and to supply food for both animals and humans. The high quality vegetable oil extracted from canola grain is a primary reason for canola's commercial value. Thus, in addition to breeding varieties that offer high grain yields, canola plant breeders also focus on increasing the oil content level in the grain in order to maximize total oil yield per acre. To accomplish these goals, the canola breeder must select and develop canola plants that have the traits that result in superior lines.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements According to the invention, there is provided a new canola line designated SCV425044. This invention thus relates to the seeds of canola line SCV425044, to the plants, or plant parts, of canola SCV425044 and to methods for producing a canola plant produced by crossing the canola SCV425044 with itself or another canola genotype, and the creation of variants by mutagenesis or transformation of canola SCV425044.

Thus, any such methods using the canola line SCV425044 are part of this invention: selfing, backcrosses, hybrid production, crosses to populations, and the like. All plants produced using canola line SCV425044 as a parent are within the scope of this invention. Advantageously, the canola line could be used in crosses with other, different, canola plants to produce first generation ($F_1$) canola hybrid seeds and plants with superior characteristics.

In another aspect, the present invention provides for single or multiple gene converted plants of SCV425044. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, enhanced nutritional quality, modified fatty acid metabolism, modified carbohydrate metabolism, modified seed yield, modified oil percent, modified protein percent, modified lodging resistance, modified glucosinolate content, modified chlorophyll content and industrial usage. The gene may be a naturally occurring canola gene or a transgene introduced through genetic engineering techniques.

In another aspect, the present invention provides regenerable cells for use in tissue culture of canola plant SCV425044. The tissue culture will preferably be capable of regenerating plants having essentially all of the physiological and morphological characteristics of the foregoing canola plant, and of regenerating plants having substantially the same genotype as the foregoing canola plant. Preferably, the regenerable cells in such tissue cultures will be embryos, protoplasts, meristematic cells, callus, pollen, leaves, anthers, pistils, cotyledons, roots, root tips, flowers, seeds, pods or stems. Still further, the present invention provides canola plants regenerated from the tissue cultures of the invention.

In another aspect, the present invention provides a method of introducing a desired trait into canola line SCV425044 wherein the method comprises crossing a SCV425044 plant with a plant of another canola genotype that comprises a desired trait to produce F$_1$ progeny plants, wherein the desired trait is selected from the group consisting of male sterility, herbicide resistance, insect resistance, modified fatty acid metabolism, modified carbohydrate metabolism, modified seed yield, modified oil percent, modified protein percent, modified lodging resistance and resistance to bacterial disease, fungal disease or viral disease; selecting one or more progeny plants that have the desired trait to produce selected progeny plants; crossing the selected progeny plants with the SCV425044 plants to produce backcross progeny plants; selecting for backcross progeny plants that have the desired trait and essentially all of the physiological and morphological characteristics of canola line SCV425044 to produce selected backcross progeny plants; and repeating these steps three or more times to produce selected fourth or higher backcross progeny plants that comprise the desired trait and essentially all of the physiological and morphological characteristics of canola line SCV425044 as listed in Table 1. Included in this aspect of the invention is the plant produced by the method wherein the plant has the desired trait and essentially all of the physiological and morphological characteristics of canola line SCV425044 as listed in Table 1.

In addition to the exemplary aspects and embodiments described above, further aspects and embodiments will become apparent by study of the following descriptions.

Definitions

In the description and tables which follow, a number of terms are used. In order to provide a clear and consistent understanding of the specification and claims, including the scope to be given such terms, the following definitions are provided:

Allele. Allele is any of one or more alternative forms of a gene which relate to one trait or characteristic. In a diploid cell or organism, the two alleles of a given gene occupy corresponding loci on a pair of homologous chromosomes.

Alter. The utilization of up-regulation, down-regulation, or gene silencing.

Anther arrangement. The orientation of the anthers in fully opened flowers can also be useful as an identifying trait. This can range from introse (facing inward toward pistil), erect (neither inward not outward), or extrose (facing outward away from pistil).

Anther dotting. The presence/absence of anther dotting (colored spots on the tips of anthers) and if present, the percentage of anther dotting on the tips of anthers in newly opened flowers is also a distinguishing trait for varieties.

Anther fertility. This is a measure of the amount of pollen produced on the anthers of a flower. It can range from sterile (such as in female parents used for hybrid seed production) to fertile (all anthers shedding).

Backcrossing. Backcrossing is a process in which a breeder repeatedly crosses hybrid progeny back to one of the parents, for example, a first generation hybrid F$_1$ with one of the parental genotypes of the F$_1$ hybrid.

Blackleg (*Leptosphaeria maculans*). Virulent or severe blackleg of canola/rapeseed is a fungal canker or dry rot disease of the actively growing crop that causes stem girdling and lodging. In heavily infested crops, up to 100 percent of the stems may be infected, resulting in major yield loss. For purposes of this application, resistance to blackleg is measured using ratings of "R" (resistant), "MR" (medium resistant), "MS" (moderately susceptible) or "S" (susceptible).

Cell. Cell as used herein includes a plant cell, whether isolated, in tissue culture or incorporated in a plant or plant part.

Cotyledon width. The cotyledons are leaf structures that form in the developing seeds of canola which make up the majority of the mature seed of these species. When the seed germinates, the cotyledons are pushed out of the soil by the growing hypocotyls (segment of the seedling stem below the cotyledons and above the root) and they unfold as the first photosynthetic leafs of the plant. The width of the cotyledons varies by variety and can be classified as narrow, medium, or wide.

Elite canola line. A canola line, per se, which has been sold commercially.

Elite canola parent line. A canola line which is the parent line of a canola hybrid which has been commercially sold.

Embryo. The embryo is the small plant contained within a mature seed.

Essentially all of the physiological and morphological characteristics. "Essentially all of the physiological and morphological characteristics" refers to a plant having essentially all of the physiological and morphological characteristics of the recurrent parent, except for the characteristics derived from the converted trait.

FAME analysis. Fatty Acid Methyl Ester analysis is a method that allows for accurate quantification of the fatty acids that make up complex lipid classes.

Flower bud location. The location of the unopened flower buds relative to the adjacent opened flowers is useful in distinguishing between the canola species. The unopened buds are held above the most recently opened flowers in *B. napus* and they are positioned below the most recently opened flower buds in *B. rapa*.

Flowering date. This is measured by the number of days from planting to the stage when 50% of the plants in a population have one or more open flowers. This varies from variety to variety.

*Fusarium* Wilt. *Fusarium* wilt, largely caused by *Fusarium oxysporum*, is a disease of canola that causes part or all of a plant to wilt, reducing yield by up to 30% or more on badly affected fields. For purposes of this application, resistance to *Fusarium* wilt is measured using ratings of "R" (resistant), "MR" (medium resistant), "MS" (moderately susceptible) or "S" (susceptible).

Gene silencing. Gene silencing means the interruption or suppression of the expression of a gene at the level of transcription or translation.

Genotype. Refers to the genetic constitution of a cell or organism.

Glucosinolates. These are measured in micromoles (μm) of total alipathic glucosinolates per gram of air-dried oil-free meal. The level of glucosinolates is somewhat influenced by the sulfur fertility of the soil, but is also controlled by the genetic makeup of each variety and thus can be useful in characterizing varieties.

Growth habit. At the end of flowering, the angle relative to the ground surface of the outermost fully expanded leaf petioles is a variety specific trait. This trait can range from erect (very upright along the stem) to prostrate (almost horizontal and parallel with the ground surface).

Leaf attachment to the stem. This trait is especially useful for distinguishing between the two canola species. The base of the leaf blade of the upper stem leaves of *B. rapa* completely clasp the stem whereas those of the *B. napus* only partially clasp the stem. Those of the mustard species do not clasp the stem at all.

Leaf blade color. The color of the leaf blades is variety specific and can range from light to medium dark green to blue green.

Leaf development of lobes. The leaves on the upper portion of the stem can show varying degrees of development of lobes which are disconnected from one another along the petiole of the leaf. The degree of lobing is variety specific and can range from absent (no lobes)/weak through very strong (abundant lobes).

Leaf glaucosity. This refers to the waxiness of the leaves and is characteristic of specific varieties although environment can have some effect on the degree of waxiness. This trait can range from absent (no waxiness)/weak through very strong. The degree of waxiness can be best determined by rubbing the leaf surface and noting the degree of wax present.

Leaf indentation of margin. The leaves on the upper portion of the stem can also show varying degrees of serration along the leaf margins. The degree of serration or indentation of the leaf margins can vary from absent (smooth margin)/weak to strong (heavy saw-tooth like margin).

Leaf pubescence. The leaf pubescence is the degree of hairiness of the leaf surface and is especially useful for distinguishing between the canola species. There are two main classes of pubescence which are glabrous (smooth/not hairy) and pubescent (hairy) which mainly differentiate between the *B. napus* and *B. rapa* species, respectively.

Leaf surface. The leaf surface can also be used to distinguish between varieties. The surface can be smooth or rugose (lumpy) with varying degrees between the two extremes.

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging resistance. Lodging is rated on a scale of 1 to 5. A score of 1 indicates erect plants. A score of 5 indicates plants are lying on the ground Maturity. The maturity of a variety is measured as the number of days between planting and physiological maturity. This is useful trait in distinguishing varieties relative to one another.

Oil content. This is measured as percent of the whole dried seed and is characteristic of different varieties. It can be determined using various analytical techniques such as NMR, NIR, and Soxhlet extraction.

Percent linolenic acid. Percent oil of the seed that is linolenic acid.

Percent oleic acid (OLE). Percent oil of the seed that is oleic acid.

Percentage of total fatty acids. This is determined by extracting a sample of oil from seed, producing the methyl esters of fatty acids present in that oil sample and analyzing the proportions of the various fatty acids in the sample using gas chromatography. The fatty acid composition can also be a distinguishing characteristic of a variety.

Petal color. The petal color on the first day a flower opens can be a distinguishing characteristic for a variety. It can be white, varying shades of yellow or orange.

Plant. As used herein, the term "plant" includes reference to an immature or mature whole plant, including a plant from which seed or grain or anthers have been removed. Seed or embryo that will produce the plant is also considered to be the plant.

Plant height. This is the height of the plant at the end of flowering if the floral branches are extended upright (i.e., not lodged). This varies from variety to variety and although it can be influenced by environment, relative comparisons between varieties grown side by side are useful for variety identification.

Plant parts. As used herein, the term "plant parts" (or a canola plant, or a part thereof) includes protoplasts, leaves, stems, roots, root tips, anthers, pistils, seed, grain, embryo, pollen, ovules, cotyledon, hypocotyl, pod, flower, shoot, tissue, petiole, cells, meristematic cells and the like.

Protein content. This is measured as percent of whole dried seed and is characteristic of different varieties. This can be determined using various analytical techniques such as NIR and Kjeldahl.

Quantitative trait loci (QTL). Quantitative trait loci (QTL) refer to genetic loci that control to some degree numerically representable traits that are usually continuously distributed.

Regeneration. Regeneration refers to the development of a plant from tissue culture.

Resistance to lodging. This measures the ability of a variety to stand up in the field under high yield conditions and severe environmental factors. A variety can have good (remains upright), fair, or poor (falls over) resistance to lodging. The degree of resistance to lodging is not expressed under all conditions but is most meaningful when there is some degree of lodging in a field trial.

Seed coat color. The color of the seed coat can be variety specific and can range from black through brown through yellow. Color can also be mixed for some varieties.

Seed coat mucilage. This is useful for differentiating between the two species of canola with *B. rapa* varieties having mucilage present in their seed coats whereas *B. napus* varieties do not have this present. It is detected by imbibing seeds with water and monitoring the mucilage that is exuded by the seed.

Seedling growth habit. The rosette consists of the first 2-8 true leaves and a variety can be characterized as having a strong rosette (closely packed leaves) or a weak rosette (loosely arranged leaves).

Silique (pod) habit. This is also a trait which is variety specific and is a measure of the orientation of the pods along the racemes (flowering stems). This trait can range from erect (pods angled close to racemes) through horizontal (pods perpendicular to racemes) through arching (pods show distinct arching habit).

Silique (pod) length of beak. The beak is the segment at the end of the pod which does not contain seed (it is a remnant of the stigma and style for the flower). The length of the beak can be variety specific and can range form short through medium through long.

Silique (pod) length of pedicel. The pedicel is the stem that attaches the pod to the raceme of flowering shoot. The length of the pedicel can be variety specific and can vary from short through medium through long.

Silique (pod) length. This is the length of the fully developed pods and can range from short to medium to long. It is best used by making comparisons relative to reference varieties.

Silique (pod) type. This is typically a bilateral single pod for both species of canola and is not really useful for variety identification within these species.

Silique (pod) width. This is the width of the fully developed pods and can range from narrow to medium to wide. It is best used by making comparisons relative to reference varieties.

Single gene converted (conversion). Single gene converted (conversion) plant refers to plants which are developed by a plant breeding technique called backcrossing, or via genetic engineering, wherein essentially all of the desired morphological and physiological characteristics of a variety are recovered in addition to the single gene transferred into the variety via the backcrossing technique or via genetic engineering.

Stem intensity of anthocyanin coloration. The stems and other organs of canola plants can have varying degrees of purple coloration which is due to the presence of anthocyanin (purple) pigments. The degree of coloration is somewhat subject to growing conditions, but varieties typically show varying degrees of coloration ranging from: absent (no purple)/very weak to very strong (deep purple coloration).

Total saturated (TOTSAT). Total percent oil of the seed of the saturated fats in the oil including C12:0, C14:0, C16:0, C18:0, C20:0, C22:0 and C24.0.

DETAILED DESCRIPTION OF THE INVENTION

SCV425044 is a ROUNDUP READY™ pollen fertile canola maintainer inbred line (B-line) used for producing hybrids with resistance to blackleg and *fusarium* wilt. Canola line SCV425044 is stable, uniform and no off-type plants have been exhibited in evaluation. Some of the criteria used for selection in various generations include: sterility, ROUNDUP READY™ trait, standability, combining ability, oil content, maturity and total saturated fats.

The line has shown uniformity and stability, as described in the following variety description information. It has been self-pollinated a sufficient number of generations with careful attention to uniformity of plant type. The line has been increased with continued observation for uniformity.

Canola line SCV425044 has the following morphologic and other characteristics.

TABLE 1

VARIETY DESCRIPTION INFORMATION
PLANT:

| | |
|---|---|
| Maturity: | Earlier than cultivars 46A65 and Q2 |
| Height: | Slightly taller than 46A65 and Q2 |
| Lodging: | Slightly less lodging vs. 46A65 and Q2 |
| Herbicide resistance: | Resistant to ROUNDUP READY ™ herbicides |
| Diseases: | |
| Blackleg (*Leptosphaeria maculans*): | Resistant (R) |
| *Fusarium* Wilt: | Resistant (R) |
| Seed Characteristics: | |
| Coat color: | Dark brown to black |
| Oil content (% whole seed @ 8.5% moisture): | Higher than 46A65 and Q2 |
| Protein content (% defatted, dry meal): | Higher than 46A65 and Q2 |

TABLE 1-continued

VARIETY DESCRIPTION INFORMATION
PLANT:

| | |
|---|---|
| Erucic acid content in oil: | Less than 0.2% |
| Glucosinolate content: | Lower than 46A65 and Q2 |

This invention is also directed to methods for producing a canola plant by crossing a first parent canola plant with a second parent canola plant, wherein the first or second canola plant is the canola plant from the line SCV425044. Further, both first and second parent canola plants may be from the line SCV425044. Therefore, any methods using the line SCV425044 are part of this invention: selfing, backcrosses, hybrid breeding, and crosses to populations. Any plants produced using line SCV425044 as a parent are within the scope of this invention.

Additional methods include, but are not limited to, expression vectors introduced into plant tissues using a direct gene transfer method such as microprojectile-mediated delivery, DNA injection, electroporation and the like. More preferably, expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

FURTHER EMBODIMENTS OF THE INVENTION

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species which are inserted into the genome using transformation, are referred to herein collectively as "transgenes". In some embodiments of the invention, a transgenic variant of SCV425044 may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed canola line SCV425044.

One embodiment of the invention is a process for producing canola line SCV425044 further comprising a desired trait, said process comprising transforming a canola plant of line SCV425044 with a transgene that confers a desired trait. Another embodiment is the product produced by this process. In one embodiment the desired trait may be one or more of herbicide resistance, insect resistance, disease resistance, modified seed yield, modified oil percent, modified protein percent, modified lodging resistance or modified fatty acid or carbohydrate metabolism. The specific gene may be any known in the art or listed herein, including; a polynucleotide conferring resistance to imidazolinone, sulfonylurea, glyphosate, glufosinate, triazine, hydroxyphenylpyruvate dioxygenase inhibitor, protoporphyrinogen oxidase inhibitor and benzonitrile; a polynucleotide encoding a *Bacillus thuringiensis* polypeptide, a polynucleotide encoding phytase, FAD-2, FAD-3, galactinol synthase or a raffinose synthetic enzyme; or a polynucleotide conferring resistance to blackleg, white rust or other common canola diseases.

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Genetic Transformation for the Improvement of Canola World Conf., Biotechnol Fats and Oils Ind. 1988. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A genetic trait which has been engineered into the genome of a particular canola plant may then be moved into the genome of another variety using traditional breeding techniques that are well known in the plant breeding arts. For example, a backcrossing approach is commonly used to move a transgene from a transformed canola variety into an already developed canola variety, and the resulting backcross conversion plant would then comprise the transgene(s).

Various genetic elements can be introduced into the plant genome using transformation. These elements include, but are not limited to genes, coding sequences, inducible, constitutive, and tissue specific promoters, enhancing sequences, and signal and targeting sequences. For example, see the traits, genes and transformation methods listed in U.S. Pat. No. 6,118,055.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed canola plants, using transformation methods as described below to incorporate transgenes into the genetic material of the canola plant(s).

Expression Vectors for Canola Transformation

Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase and the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci. U.S.A.* 84:131 (1987), DeBlock et al., *EMBO J.* 3:1681 (1984).

In vivo methods for visualizing GUS activity that do not require destruction of plant tissue are available. Molecular Probes publication 2908, IMAGENE GREENJ, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Canola Transformation

Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in canola. Optionally, the inducible promoter is operably linked to a nucleotide sequence encoding a signal sequence which is operably linked to a gene for expression in canola. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters—A constitutive promoter is operably linked to a gene for expression in canola or the constitutive promoter is operably linked to a nucleotide sequence encoding a signal sequence which is operably linked to a gene for expression in canola.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT application WO 96/30530.

C. Tissue-specific or Tissue-preferred Promoters—A tissue-specific promoter is operably linked to a gene for expression in canola. Optionally, the tissue-specific promoter is operably linked to a nucleotide sequence encoding a signal sequence which is operably linked to a gene for expression in canola. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Knox, C., et al., *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., *Cell* 39:499-509 (1984), Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a canola plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology* CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Wang et al. discuss "Large Scale Identification, Mapping and Genotyping of Single-Nucleotide Polymorphisms in the Human Genome", *Science,* 280:1077-1082, 1998, and similar capabilities are becoming increasingly available for the canola genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of agronomic interest. Through the transformation of canola the expression of genes can be altered to enhance disease resistance, insect resistance, herbicide resistance, agronomic, grain quality and other traits. Transformation can also be used to insert DNA sequences which control or help control male-sterility. DNA sequences native to canola as well as non-native DNA sequences can be transformed into canola and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, *The Maize Handbook* ch. 118, Springer-Verlag, 1994) or other genetic elements such as a FRT, Lox or other site specific integration site, antisense technology (see, e.g., Sheehy et al. (1988) *PNAS USA* 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:
    A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262: 1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*), McDowell & Woffenden, (2003) *Trends Biotechnol.* 21(4): 178-83 and Toyoda et al., (2002) *Transgenic Res.* 11 (6):567-82.
    B. A gene conferring resistance to fungal pathogens, such as oxalate oxidase or oxalate decarboxylase (Zhou et al., (1998) Pl. Physiol. 117:33-41).
    C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.
    D. A lectin. See, for example, the disclosure by Van Damme et al., *Plant Molec. Biol.* 24:25 (1994), who disclose the nucleotide sequences of several *Clivia miniata* mannose-binding lectin genes.
    E. A vitamin-binding protein such as avidin. See PCT application US93/06487. The application teaches the use of avidin and avidin homologues as larvicides against insect pests.
    F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).
    G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene, U.S. Pat. Nos. 7,145,060, 7,087,810 and 6,563,020.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology*, 5(2) (1995); Pieterse & Van Loon (2004) *Curr. Opin. Plant Bio.* 7(4): 456-64 and Somssich (2003) *Cell* 113(7):815-6.

U. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2):137-149 (1998). Also see U.S. Pat. No. 6,875,907.

V. Detoxification genes, such as for fumonisin, beauvericin, moniliformin and zearalenone and their structurally related derivatives. For example, see U.S. Pat. No. 5,792,931.

W. Cystatin and cysteine proteinase inhibitors. See U.S. Pat. No. 7,205,453.

X. Defensin genes. See WO 03/000863 and U.S. Pat. No. 6,911,577.

Y. Genes that confer resistance to *Phytophthora* root rot, such as the *Brassica* equivalents of the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes That Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvylshikimate-3-phosphate synthase (EPSP) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. U.S. Pat. No. 5,627,061 to Barry et al. also describes genes encoding EPSPS enzymes. See also U.S. Pat. Nos. 6,566,587; 6,338, 961; 6,248,876 B1; 6,040,497; 5,804,425; 5,633,435; 5,145,783; 4,971,908; 5,312,910; 5,188,642; 4,940, 835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. No. 10/427,692. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin.

The nucleotide sequence of a PAT gene is provided in European application No. 0 242 246 to Leemans et al., DeGreef et al., *Bio/Technology* 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285: 173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes That Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which is responsible for maize mutants characterized by low levels of phytic acid. See Raboy et al., *Maydica* 35:383 (1990) and/or by altering inositol kinase activity as in WO 02/059324, U.S. Pat. No. 7,067,720, WO 03/027243, US2003/0079247, WO 99/05298, U.S. Pat. No. 6,197,561, U.S. Pat. No. 6,291,224, U.S. Pat. No. 6,391,348, WO 2002/059324, WO 98/45448, WO 99/55882, WO 01/04147.

C. Modified carbohydrate composition effected, for example, by transforming plants with a gene coding for an enzyme that alters the branching pattern of starch, or, a gene altering thioredoxin such as NTR and/or TRX (See U.S. Pat. No. 6,531,648 which is incorporated by reference for this purpose) and/or a gamma zein knock out or mutant such as cs27 or TUSC27 or en27 (See U.S. Pat. No. 6,858,778 and U.S. Patent Publication Nos. US2005/0160488, US2005/0204418; which are incorporated by reference for this purpose). See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* alpha-amylase), Elliot et al., *Plant Molec. Biol.* 21: 515 (1993) (nucleotide sequences of tomato invertase genes), Sogaard et al., *J. Biol. Chem.* 268: 22480 (1993) (site-directed mutagenesis of barley alpha-amylase gene), and Fisher et al., *Plant Physiol.* 102: 1045 (1993) (maize endosperm starch branching enzyme II), WO 99/10498 (improved digestibility and/or starch extraction through modification of UDP-D-xylose 4-epimerase, Fragile 1 and 2, Ref 1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.
D. Elevated oleic acid via FAD-2 gene modification and/or decreased linolenic acid via FAD-3 gene modification. See U.S. Pat. Nos. 6,063,947; 6,323,392; and international publication WO 93/11245.
E. Altering conjugated linolenic or linoleic acid content, such as in WO 01/12800. Altering LEC1, AGP, Dek1, Superal1, milps, various Ipa genes such as Ipa1, Ipa3, hpt or hggt. For example, see WO 02/42424, WO 98/22604, WO 03/011015, U.S. Pat. Nos. 6,423,886, 6,197,561, 6,825,397, 7,157,621, U.S. Patent Publication 2003/0079247, International publications WO 02/057439 and WO 03/011015 and Rivera-Madrid, R. et al. *Proc. Natl. Acad. Sci.* 92:5620-5624 (1995).
F. Altered antioxidant content or composition, such as alteration of tocopherol or tocotrienols. For example, see U.S. Pat. Nos. 6,787,683 and 7,154,029 and WO 00/68393 involving the manipulation of antioxidant levels through alteration of a phytl prenyl transferase (ppt), WO 03/082899 through alteration of a homogentisate geranyl geranyl transferase (hggt).
G. Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 99/40209 (alteration of amino acid compositions in seeds), WO 99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885, 801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 98/56935 (plant amino acid biosynthetic enzymes), WO 98/45458 (engineered seed protein having higher percentage of essential amino acids), WO 98/42831 (increased lysine), U.S. Pat. No. 5,633,436 (increasing sulfur amino acid content), U.S. Pat. No. 5,559, 223 (synthetic storage proteins with defined structure containing programmable levels of essential amino acids for improvement of the nutritional value of plants), WO 96/01905 (increased threonine), WO 95/15392 (increased lysine), U.S. Pat. Nos. 6,930, 225, 7,179,955, U.S. Publication No. 2004/0068767, U.S. Pat. No. 6,803,498, WO 01/79516, and WO 00/09706 (Ces A: cellulose synthase), U.S. Pat. No. 6,194,638 (hemicellulose), U.S. Pat. No. 6,399,859 and U.S. Pat. No. 7,098,381 (UDPGdH), U.S. Pat. No. 6,194,638 (RGP).
4. Genes that Control Male Sterility
There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.
A. Introduction of a deacetylase gene under the control of a tapetum-specific promoter and with the application of the chemical N—Ac-PPT. See international publication WO 01/29237.
B. Introduction of various stamen-specific promoters. See international publications WO 92/13956 and WO 92/13957.
C. Introduction of the barnase and the barstar genes. See Paul et al., *Plant Mol. Biol.* 19:611-622, 1992).
For additional examples of nuclear male and female sterility systems and genes, see also, U.S. Pat. Nos. 5,859,341; 6,297,426; 5,478,369; 5,824,524; 5,850, 014; and 6,265,640; all of which are hereby incorporated by reference.
5. Genes that Create a Site for Site Specific DNA Integration
This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118, Springer-Verlag, 1994), the Pin recombinase of *E. coli* (Enomoto et al., 1983), and the R/RS system of the pSR1 plasmid (Araki et al., 1992).
6. Genes that Affect Abiotic Stress Resistance
Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717, 034, 6,801,104, international patent publications WO 2000/060089, WO 2001/026459, WO 2001/035725, WO 2001/034726, WO 2001/035727, WO 2001/ 036444, WO 2001/036597, WO 2001/036598, WO 2002/015675, WO 2002/017430, WO 2002/077185, WO 2002/079403, WO 2003/013227, WO 2003/ 013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Patent Publication 2004/0148654 and international publication WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield. Also see WO 02/02776, WO 2003/052063, JP2002281975, U.S. Pat. No. 6,084,153, WO 01/64898, U.S. Pat. Nos. 6,177,275 and 6,107,547 (enhancement of nitrogen utilization and altered nitrogen responsiveness). For ethylene alteration, see US 2004/0128719, US 2003/0166197 and WO 2000/32761. For plant transcription factors or transcriptional regulators of abiotic stress, see e.g. US 2004/0098764 or US 2004/0078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), U.S. Pat. No. 6,794,560, 6,307,126 (GAI), WO 96/14414 (CON), WO 96/38560, WO 01/21822 (VRN1), WO 00/44918 (VRN2), WO 99/49064 (GI), WO 00/46358 (FR1), WO 97/29123, WO 99/09174 (D8 and Rht), and WO 2004/076638 and WO 2004/031349 (transcription factors).

Methods for Canola Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of canola target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular canola line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For exemplary methodologies, see Glick et al., 1993. *Methods in Plant Molecular Biology and Biotechnology*. CRC Press, Boca Raton.

Particular markers used for these purposes are not limited to any particular set of markers, but are envisioned to include any type of marker and marker profile which provides a means of distinguishing varieties. One method of comparison is to use only homozygous loci for SCV425044.

In addition to being used for identification of canola line SCV425044 and plant parts and plant cells of line SCV425044, the genetic profile may be used to identify a canola plant produced through the use of SCV425044 or to verify a pedigree for progeny plants produced through the use of SCV425044. The genetic marker profile is also useful in breeding and developing backcross conversions.

The present invention comprises a canola plant characterized by molecular and physiological data obtained from the representative sample of said variety deposited with the American Type Culture Collection (ATCC). Further provided by the invention is a canola plant formed by the combination of the disclosed canola plant or plant cell with another canola plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology. For example, see Batley, J. et al. 2007. *Mol. Ecol. Notes* (OnlineEarly Articles) and Plieske, J. et al., 2001. *Theor. Appl. Genet.* 102:689-694.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

The SSR profile of canola plant SCV425044 can be used to identify plants comprising SCV425044 as a parent, since such plants will comprise the same homozygous alleles as SCV425044. Because the canola variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of SCV425044 in their development, such as SCV425044 comprising a backcross conversion, transgene, or genetic sterility factor, may be identified by having a molecular marker profile with a high percent identity to SCV425044. Such a percent identity might be 95%, 96%, 97%, 98%, 99%, 99.5% or 99.9% identical to SCV425044.

The SSR profile of SCV425044 also can be used to identify essentially derived varieties and other progeny varieties developed from the use of SCV425044, as well as cells and other plant parts thereof. Such plants may be developed using the markers identified in WO 00/31964, U.S. Pat. No. 6,162,967 and U.S. application Ser. No. 09/954,773. Progeny plants and plant parts produced using SCV425044 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from canola variety, as measured by either percent identity or percent similarity. Such progeny may be further characterized as being within a pedigree distance of SCV425044, such as within 1, 2, 3, 4 or 5 or less cross-pollinations to a canola plant other than SCV425044 or a plant that has SCV425044 as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Single-Gene Conversions

When the term "canola plant" is used in the context of the present invention, this also includes any single gene conversions of that variety. The term single gene converted plant as used herein refers to those canola plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental canola plant that contributes the gene for the desired characteristic is termed the nonrecurrent or donor parent. This terminology refers to the fact that the nonrecurrent parent is used one time in the backcross protocol and therefore does not recur. The parental canola plant to which the gene or genes from the nonrecurrent parent are transferred is known as the recurrent parent as it is used for several rounds in the backcrossing protocol (Poehlman & Sleper, 1994; Fehr, *Principles of Cultivar Development* (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a canola plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic; examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445; the disclosures of which are specifically hereby incorporated by reference.

Introduction of a New Trait or Locus Into SCV425044

Line SCV425044 represents a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of SCV425044

A backcross conversion of SCV425044 occurs when DNA sequences are introduced through backcrossing with SCV425044 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: *Proceedings Symposium of the Analysis of Molecular Data*, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in *Corn and Corn Improvement*, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, altered seed amino acid levels, altered seed oil levels, low phytate, industrial enhancements, disease resistance (bacterial, fungal or viral), insect resistance and herbicide resistance. In addition, an introgression site itself, such as an FRT site, Lox site or other site specific integration site, may be inserted by backcrossing and utilized for direct insertion of one or more genes of interest into a specific plant variety. In some embodiments of the invention, the number of loci that may be backcrossed into SCV425044 is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, P. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

One process for adding or modifying a trait or locus in canola line SCV425044 comprises crossing SCV425044 plants grown from SCV425044 seed with plants of another canola variety that comprise the desired trait or locus, selecting $F_1$ progeny plants that comprise the desired trait or locus to produce selected $F_1$ progeny plants, crossing the selected progeny plants with the SCV425044 plants to produce backcross progeny plants, selecting for backcross progeny plants that have the desired trait or locus and the morphological characteristics of canola line SCV425044 to produce selected backcross progeny plants; and backcrossing to SCV425044 three or more times in succession to produce selected fourth or higher backcross progeny plants that comprise said trait or locus. The modified SCV425044 may be further characterized as having essentially all of the physiological and morphological characteristics of canola line SCV425044 listed in Table 1 and/or may be characterized by percent similarity or identity to SCV425044 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox and other sites for site specific integration, which may also affect a desired trait if a functional nucleic acid is inserted at the integration site.

In addition, the above process and other similar processes described herein may be used to produce first generation progeny canola seed by adding a step at the end of the process that comprises crossing SCV425044 with the introgressed trait or locus with a different canola plant and harvesting the resultant first generation progeny canola seed.

Tissue Culture of Canola

Further production of the SCV425044 line can occur by tissue culture and regeneration. Tissue culture of various tissues of canola and regeneration of plants therefrom is known and widely published. For example, reference may be had to Chuong et al., "A Simple Culture Method for *Brassica* Hypocotyl Protoplasts", *Plant Cell Reports* 4:4-6 (1985); Barsby, T. L., et al., "A Rapid and Efficient Alternative Procedure for the Regeneration of Plants from Hypocotyl Protoplasts of *Brassica napus*", *Plant Cell Reports*, (Spring, 1996); Kartha, K., et al., "In vitro Plant Formation from Stem Explants of Rape", *Physiol. Plant,* 31:217-220 (1974); Narasimhulu, S., et al., "Species Specific Shoot Regeneration Response of Cotyledonary Explants of *Brassicas*", *Plant Cell Reports*, (Spring 1988); Swanson, E., "Microspore Culture in *Brassica*", *Methods in Molecular Biology*, Vol. 6, Chapter 17, p. 159 (1990). Thus, another aspect of this invention is to provide cells which upon growth and differentiation produce canola plants having the physiological and morphological characteristics of canola line SCV425044.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, describe certain techniques, the disclosures of which are incorporated herein by reference for this purpose.

Using SCV425044 to Develop Other Canola Varieties

Canola varieties such as SCV425044 are typically developed for use in seed and grain production. However, canola varieties such as SCV425044 also provide a source of breeding material that may be used to develop new canola varieties. Plant breeding techniques known in the art and used in a canola plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of canola varieties in a plant breeding program requires, in general, the development and evaluation of homozygous varieties. For a general description of rapeseed and canola breeding, see Downey et al., 1987. Rapeseed and Mustard in Fehr, W. R. (ed.), *Principles of Cultivar Development* p. 437-486. N.Y., Macmillan and Co.; Thompson, K. F., 1983. Breeding winter oilseed rape *Brassica napus. Adv. Appl. Bio.* 7:1-104; and Ward, et al., 1985. *Oilseed Rape*. Farming Press Ltd., Wharefedale Road, Ipswich, Suffolk.

Additional Breeding Methods

This invention is directed to methods for producing a canola plant by crossing a first parent canola plant with a second parent canola plant wherein either the first or second parent canola plant is line SCV425044. The other parent may be any other canola plant, such as a canola plant that is part of a synthetic or natural population. Any such methods using canola line SCV425044 are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, *Principles of Plant Breeding*, 1960; Simmonds, *Principles of Crop Improvement,* 1979; Sneep et al., 1979).

The following describes breeding methods that may be used with canola line SCV425044 in the development of further canola plants. One such embodiment is a method for developing a line SCV425044 progeny canola plant in a canola plant breeding program comprising: obtaining the canola plant, or a part thereof, of line SCV425044 utilizing said plant or plant part as a source of breeding material and selecting a canola line SCV425044 progeny plant with molecular markers in common with line SCV425044 and/or with morphological and/or physiological characteristics selected from the characteristics listed in Table 1. Breeding steps that may be used in the canola plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of canola line SCV425044 progeny canola plants, comprising crossing line SCV425044 with another canola plant, thereby producing a population of canola plants, which, on average, derive 50% of their alleles from canola line SCV425044. A plant of this population may be selected and repeatedly selfed or sibbed with a canola line resulting from these successive filial generations. One embodiment of this invention is the canola line produced by this method and that has obtained at least 50% of its alleles from canola line SCV425044.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987).

Thus the invention includes canola line SCV425044 progeny canola plants comprising a combination of at least two line SCV425044 traits selected from the group consisting of those listed in Table 1 or the line SCV425044 combination of traits listed in the Summary of the Invention, so that said progeny canola plant is not significantly different for said traits than canola line SCV425044 as determined at the 5% significance level when grown in the same environmental conditions. Using techniques described herein, molecular markers may be used to identify said progeny plant as a canola line SCV425044 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of canola line SCV425044 may also be characterized through their filial relationship with canola line SCV425044, as for example, being within a certain number of breeding crosses of canola line SCV425044. A breeding cross is a cross made to introduce new genetics into the progeny, and is distinguished from a cross, such as a self or a sib cross, made to select among existing genetic alleles. The lower the number of breeding crosses in the pedigree, the closer the relationship between canola line SCV425044 and its progeny. For example, progeny produced by the methods described herein may be within 1, 2, 3, 4 or 5 breeding crosses of canola line SCV425044.

As used herein, the term "plant" includes plant cells, plant protoplasts, plant cell tissue cultures from which canola plants can be regenerated, plant calli, plant clumps, and plant cells that are intact in plants or parts of plants, such as embryos, pollen, ovules, flowers, pods, leaves, roots, root tips, anthers, cotyledons, hypocotyls, meristematic cells, stems, pistils, petiole, and the like.

Pedigree Breeding

Pedigree breeding starts with the crossing of two genotypes, such as SCV425044 and another canola variety having one or more desirable characteristics that is lacking or which complements SCV425044. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a canola variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new canola varieties.

Therefore, an embodiment of this invention is a method of making a backcross conversion of canola line SCV425044, comprising the steps of crossing a plant of canola line SCV425044 with a donor plant comprising a desired trait, selecting an $F_1$ progeny plant comprising the desired trait, and backcrossing the selected $F_1$ progeny plant to a plant of canola line SCV425044. This method may further comprise the step of obtaining a molecular marker profile of canola line SCV425044 and using the molecular marker profile to select for a progeny plant with the desired trait and the molecular marker profile of SCV425044. In one embodiment the desired trait is a mutant gene or transgene present in the donor parent.

Recurrent Selection and Mass Selection

Recurrent selection is a method used in a plant breeding program to improve a population of plants. SCV425044 is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation Breeding

Mutation breeding is another method of introducing new traits into canola line SCV425044. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, 1993. *Principles of Cultivar Development*, Macmillan Publishing Company. In addition, mutations created in other canola plants may be used to produce a backcross conversion of canola line SCV425044 that comprises such mutation.

Breeding with Molecular Markers

Molecular markers, which include markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing canola line SCV425044. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a canola plant for which canola line SCV425044 is a parent can be used to produce double haploid plants. Double haploids are produced by the doubling of a set of chromosomes (1 N) from a heterozygous plant to produce a completely homozygous individual. For example, see Wan et al., (1989) "Efficient Production of Doubled Haploid Plants Through Colchicine Treatment of Anther-Derived Maize Callus", *Theor. Appl. Genet.*, 77:889-892 and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. Methods for obtaining haploid plants are also disclosed in Kobayashi, M. et al., J. Heredity 71(1):9-14, 1980, Pollacsek, M., Agronomie (Paris) 12(3):247-251, 1992; Cho-Un-Haing et al., *J Plant Biol.*, 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, *Maize Genet Coop. Newsletter* 68:47; Chalyk, S.

Thus, an embodiment of this invention is a process for making a substantially homozygous SCV425044 progeny plant by producing or obtaining a seed from the cross of SCV425044 and another canola plant and applying double haploid methods to the $F_1$ seed or $F_1$ plant or to any successive filial generation. Based on studies in maize and currently being conducted in canola, such methods would decrease the number of generations required to produce a variety with similar genetics or characteristics to SCV425044. See Bernardo, R. and Kahler, A. L., *Theor. Appl. Genet.* 102:986-992, 2001.

In particular, a process of making seed retaining the molecular marker profile of canola line SCV425044 is contemplated, such process comprising obtaining or producing $F_1$ seed for which canola line SCV425044 is a parent, inducing doubled haploids to create progeny without the occurrence of meiotic segregation, obtaining the molecular marker profile of canola line SCV425044, and selecting progeny that retain the molecular marker profile of SCV425044.

A pollination control system and effective transfer of pollen from one parent to the other offers improved plant breeding and an effective method for producing hybrid canola seed and plants. For example, the ogura cytoplasmic male sterility (cms) system, developed via protoplast fusion between radish (*Raphanus sativus*) and rapeseed (*Brassica napus*) is one of the most frequently used methods of hybrid production. It provides stable expression of the male sterility trait (Ogura 1968), Pelletier et al. (1983) and an effective nuclear restorer gene (Heyn 1976).

In developing improved new *Brassica* hybrid varieties, breeders use self-incompatible (SI), cytoplasmic male sterile (CMS) and nuclear male sterile (NMS) *Brassica* plants as the female parent. In using these plants, breeders are attempting to improve the efficiency of seed production and the quality of the $F_1$ hybrids and to reduce the breeding costs. When hybridization is conducted without using SI, CMS or NMS plants, it is more difficult to obtain and isolate the desired traits in the progeny ($F_1$ generation) because the parents are capable of undergoing both cross-pollination and self-pollination. If one of the parents is a SI, CMS or NMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

In one instance, production of $F_1$ hybrids includes crossing a CMS *Brassica* female parent, with a pollen producing male *Brassica* parent. To reproduce effectively, however, the male parent of the $F_1$ hybrid must have a fertility restorer gene (Rf gene). The presence of an Rf gene means that the $F_1$ generation will not be completely or partially sterile, so that either self-pollination or cross pollination may occur. Self pollination of the $F_1$ generation to produce several subsequent generations is important to ensure that a desired trait is heritable and stable and that a new variety has been isolated.

An example of a *Brassica* plant which is cytoplasmic male sterile and used for breeding is ogura (OGU) cytoplasmic male sterile (R. Pellan-Delourme et al., 1987). A fertility restorer for ogura cytoplasmic male sterile plants has been transferred from *Raphanus sativus* (radish) to *Brassica* by Instit. National de Recherche Agricole (INRA) in Rennes, France (Pelletier et al., 1987). The restorer gene, Rf1 originating from radish, is described in WO 92/05251 and in Delourme et al., (1991). Improved versions of this restorer have been developed. For example, see WO 98/27806 "Oilseed *brassica* containing an improved fertility restorer gene for ogura cytoplasmic male sterility".

Other sources and refinements of CMS sterility in canola include the Polima cytoplasmic male sterile plant, as well as those of U.S. Pat. No. 5,789,566, "DNA sequence imparting cytoplasmic male sterility, mitochondrial genome, nuclear genome, mitochondria and plant containing said sequence and process for the preparation of hybrids"; U.S. Pat. No. 5,973,233 "Cytoplasmic male sterility system production canola hybrids"; and WO 97/02737 "Cytoplasmic male sterility system producing canola hybrids"; EP patent application 0 599042A "Methods for introducing a fertility restorer gene and for producing $F_1$ hybrids of *Brassica* plants thereby"; U.S. Pat. No. 6,229,072 "Cytoplasmic male sterility system production canola hybrids"; U.S. Pat. No. 4,658,085 "Hybridization using cytoplasmic male sterility, cytoplasmic herbicide tolerance, and herbicide tolerance from nuclear genes"; all of which are incorporated herein for this purpose.

Further, as a result of the advances in sterility systems, lines are developed that can be used as an open pollinated variety (ie. a pureline line sold to the grower for planting) and/or as a sterile inbred (female) used in the production of $F_1$ hybrid seed. In the latter case, favorable combining ability with a restorer (male) would be desirable. The resulting hybrid seed would then be sold to the grower for planting.

The development of a canola hybrid in a canola plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in canola, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line per se, is a factor in the selection of improved canola lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. Incomplete inactivation of the pollen provides the potential for self-pollination. This inadvertently self-pollinated seed may be unintentionally harvested and packaged with hybrid seed. Similarly, because the male parent is grown next to the female parent in the field there is also the potential that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in hybrid seed bags exists, the occurrence is rare because much care is taken to avoid such inclusions. These self-pollinated plants can be identified and selected by one skilled in the art, either through visual or molecular methods.

*Brassica napus* canola plants, absent the use of sterility systems, are recognized to commonly be self-fertile with approximately 70 to 90 percent of the seed normally forming as the result of self-pollination. The percentage of cross pollination may be further enhanced when populations of recognized insect pollinators at a given growing site are greater. Thus open pollination is often used in commercial canola production.

Descriptions of other breeding methods that are commonly used for different traits and crops can be found in one of several reference books (e.g., Allard, 1960; Simmonds, 1979; Sneep et al., 1979; Fehr, 1987).

Industrial Uses

Currently *Brassica napus* canola is recognized as an increasingly important oilseed crop and a source of meal in many parts of the world. The oil as removed from the seeds commonly contains a lesser concentration of endogenously formed saturated fatty acids than other vegetable oils and is well suited for use in the production of salad oil or other food products or in cooking or frying applications. The oil also finds utility in industrial applications. Additionally, the meal component of the seeds can be used as a nutritious protein concentrate for livestock.

Canola oil has the lowest level of saturated fatty acids of all vegetable oils. "Canola" refers to rapeseed (*Brassica*) which has a erucic acid ($C_{22:1}$) content of at most 2 percent by weight based on the total fatty acid content of a seed, and which produces, after crushing, an air-dried meal containing less than 30 micromoles (µmol) per gram of defatted (oil-free) meal. These types of rapeseed are distinguished by their edibility in comparison to more traditional varieties of the species.

Canola line SCV425044 can be used in the production of an edible vegetable oil or other food products in accordance with known techniques. The solid meal component derived from seeds can be used as a nutritious livestock feed. Parts of the plant not used for human or animal food can be used for biofuel.

Tables

In Table 2, selected characteristics of the seed of canola line SCV425044 are compared with seed characteristics of two commercial canola lines. The data in Table 2 includes results collected from twelve testing locations and are presented as ranges (lowest to highest) of the values observed. Column 1 shows the variety, column 2 shows the percent saturated fatty acid content, column 3 shows the percent oil content, column 4 shows the glucosinolate content in micromoles (μm) and column 5 shows the percent protein content. Compared to the two commercial canola lines 46165 and Q2, the ranges presented in Table 2 indicate that seed of canola line SCV425044 of the present invention has a percent saturated fatty acid content in a normal range, a percent oil content in a normal range, a glucosinolate content in a lower range and a percent protein content in a higher range.

TABLE 2

| 1 Variety | 2 Sat. Fats % | 3 Oil % | 4 Glucosinolate (μm) | 5 Protein % |
|---|---|---|---|---|
| SCV425044 | 6.62-6.77 | 46.73-48.20 | 11.92-15.67 | 50.93-52.40 |
| 46A65 | 6.52-6.61 | 47.21-47.88 | 16.21-16.76 | 44.72-45.76 |
| Q2 | 7.07-7.23 | 48.21-49.11 | 18.63-19.11 | 45.21-46.34 |

In Table 3, selected characteristics of a single cross hybrid (MB52141) containing canola line SCV425044 are compared with characteristics of two commercial canola lines. The comparisons in Table 3 show the deviation in values between MB52141 and the average of the two commercial canola lines, 46A65 and Q2, with the values shown being representative of data collected from a varying number of trial locations ("No. Locs"). Column 1 shows the variety, column 2 shows the percent yield deviation, column 3 shows the deviation in plant lodging ratings, column 4 shows the deviation in days to maturity, column 5 shows deviation in the percent saturated fatty acid content, column 6 shows the plant height deviation, column 7 shows the deviation in percent glucosinolate content in micromoles, column 8 shows the deviation in percent oil content, column 9 shows the deviation in percent protein content, column 10 shows the resistance rating to blackleg disease and column 11 shows the resistance rating to *Fusarium* Wilt disease.

Compared to the average of the values recorded for 46A65 and Q2, the hybrid containing SCV425044 of the present invention has higher yield, a lodging rating that is slightly decreased (less prone to lodging) but still within a normal range for commercial canola, a days to maturity rating that is 0.8 days earlier, a higher percent saturated fat content, a taller plant height, a lower percent glucosinolate content, a higher percent oil content, a higher percent protein content and comparable resistance to blackleg and *fusarium* wilt.

TABLE 3

| 1 Var. | 2 Yield % | 3 Lodging rating | 4 DMat Days | 5 Sats % | 6 Height cm | 7 Gluc % | 8 Oil % | 9 Prot % | 10 BL rating | 11 FW rating |
|---|---|---|---|---|---|---|---|---|---|---|
| MB52141* | 113.94 | −0.1 | −0.8 | +0.4 | +11.5 | −3.6 | +0.8 | +2.4 | R | R |
| No. Locs | 12 | 5 | 8 | 9 | 4 | 9 | 9 | 9 | 3 | 3 |

*Hybrid MB52141 compared to the average of commercial lines 46A65 and Q2

Deposit Information

A deposit of the Monsanto Canada Inc. proprietary canola line designated SCV425044 disclosed above and recited in the appended claims has been made with the American Type Culture Collection (ATCC), 10801 University Boulevard, Manassas, Va. 20110. The date of deposit was May 5, 2008. The deposit of 2,500 seeds was taken from the same deposit maintained by Monsanto Canada Inc. since prior to the filing date of this application. All restrictions upon the deposit have been irrevocably removed, and the deposit is intended to meet all of the requirements of 37 C.F.R. 1.801-1.809. The ATCC accession number is PTA-9195. The deposit will be maintained in the depository for a period of 30 years, or 5 years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of canola line SCV425044, representative sample of seed of which was deposited under ATCC Accession No. PTA-9195.

2. A canola plant, or a part thereof, produced by growing the seed of claim 1.

3. A tissue culture produced from protoplasts or cells from the plant of claim 2, wherein said cells or protoplasts of the tissue culture are produced from a plant part selected from the group consisting of leaf, pollen, embryo, cotyledon, hypocotyl, meristematic cell, root, root tip, anther, pistil, flower, shoot, stem, petiole and pod.

4. A canola plant regenerated from the tissue culture of claim 3, wherein the plant has essentially all of the morphological and physiological characteristics of line SCV425044 as shown in Table 1.

5. A method for producing a canola seed comprising crossing two canola plants and harvesting the resultant canola seed, wherein at least one canola plant is the canola plant of claim 2.

6. A canola seed produced by the method of claim 5.

7. A canola plant, or a part thereof, produced by growing said seed of claim 6.

8. A method for producing a male sterile canola plant wherein the method comprises transforming the canola plant of claim 2 with a nucleic acid molecule that confers male sterility.

9. A male sterile canola plant produced by the method of claim 8.

10. A method of producing an herbicide resistant canola plant wherein the method comprises transforming the canola plant of claim 2 with a transgene that confers herbicide resistance to an herbicide selected from the group consisting of imidazolinone, sulfonylurea, glyphosate, glufosinate, 2,4-D, Dicamba, L-phosphinothricin, triazine, hydroxyphenylpyruvate dioxygenase inhibitor, protoporphyrinogen oxidase inhibitor, phenoxy proprionic acid, cyclohexone and benzonitrile.

11. An herbicide resistant canola plant produced by the method of claim 10.

12. A method of producing an insect or pest resistant canola plant wherein the method comprises transforming the canola plant of claim 2 with a transgene that confers insect or pest resistance.

13. An insect or pest resistant canola plant produced by the method of claim 12.

14. The canola plant of claim 13, wherein the transgene encodes a *Bacillus thuringiensis* endotoxin.

15. A method of producing a disease resistant canola plant wherein the method comprises transforming the canola plant of claim 2 with a transgene that confers disease resistance.

16. A disease resistant canola plant produced by the method of claim 15.

17. A method of producing a canola plant with modified fatty acid metabolism or modified carbohydrate metabolism wherein the method comprises transforming the canola plant of claim 2 with a transgene encoding a protein selected from the group consisting of fructosyltransferase, levansucrase, alpha-amylase, invertase and starch branching enzyme or encoding an antisense of stearyl-ACP desaturase.

18. A canola plant having modified fatty acid metabolism or modified carbohydrate metabolism produced by the method of claim 17.

19. A canola meal from the seed of claim 1.

20. A method of introducing a desired trait into canola line SCV425044 wherein the method comprises:
   (a) crossing a SCV425044 plant, wherein a representative sample of seed was deposited under ATCC Accession No. PTA-9195, with a plant of another canola line that comprises a desired trait to produce progeny plants, wherein the desired trait is selected from the group consisting of male sterility, herbicide resistance, insect resistance, pest resistance, modified fatty acid metabolism, modified carbohydrate metabolism, modified seed yield, modified oil percent, modified protein percent, modified lodging resistance and resistance to bacterial disease, fungal disease or viral disease;
   (b) selecting one or more progeny plants that have the desired trait to produce selected progeny plants;
   (c) crossing the selected progeny plants with the SCV425044 plants to produce backcross progeny plants;
   (d) selecting for backcross progeny plants that have the desired trait and essentially all of the physiological and morphological characteristics of canola line SCV425044 listed in Table 1; and
   (e) repeating steps (c) and (d) two or more times to produce selected third or higher backcross progeny plants that comprise the desired trait and essentially all of the physiological and morphological characteristics of canola line SCV425044 as shown in Table 1.

21. A canola plant produced by the method of claim 20, wherein the plant has the desired trait.

22. The canola plant of claim 21, wherein the desired trait is herbicide resistance and the resistance is conferred to an herbicide selected from the group consisting of imidazolinone, sulfonylurea, glyphosate, glufosinate, 2,4-D, Dicamba, L-phosphinothricin, triazine, hydroxyphenylpyruvate dioxygenase inhibitor, protoporphyrinogen oxidase inhibitor, phenoxy proprionic acid, cyclohexone and benzonitrile.

23. The canola plant of claim 21, wherein the desired trait is insect resistance and the insect resistance is conferred by a transgene encoding a *Bacillus thuringiensis* endotoxin.

24. The canola plant of claim 21, wherein the desired trait is modified fatty acid metabolism or modified carbohydrate metabolism and said desired trait is conferred by a nucleic acid encoding a protein selected from the group consisting of phytase, fructosyltransferase, levansucrase, α-amylase, invertase and starch branching enzyme or encoding an antisense of stearyl-ACP desaturase.

25. A method of producing a male sterile canola plant wherein the method comprises crossing the canola plant of claim 2 with a male sterile canola plant and harvesting the resultant seed.

\* \* \* \* \*